(12) United States Patent
Wong

(10) Patent No.: US 11,766,384 B2
(45) Date of Patent: Sep. 26, 2023

(54) OBJECT-DETECTING CONTAINER APPARATUS

(71) Applicant: Aam Care, Inc., Brooklyn, NY (US)

(72) Inventor: Jiun Lang Wong, Hong Kong (HK)

(73) Assignee: Aam Care, Inc., Brooklyn, NY (US)

(*) Notice: Subject to any disclaimer, the term of this patent is extended or adjusted under 35 U.S.C. 154(b) by 414 days.

(21) Appl. No.: 17/108,573

(22) Filed: Dec. 1, 2020

(65) Prior Publication Data

US 2021/0161763 A1 Jun. 3, 2021

Related U.S. Application Data

(60) Provisional application No. 62/942,266, filed on Dec. 2, 2019.

(51) Int. Cl.
A61J 1/03 (2023.01)
G06F 3/044 (2006.01)
G16H 20/13 (2018.01)
G06F 3/041 (2006.01)
G01V 8/10 (2006.01)
G01V 3/10 (2006.01)
(Continued)

(52) U.S. Cl.
CPC .......... A61J 1/035 (2013.01); G01S 15/04 (2013.01); G01V 3/10 (2013.01); G01V 3/12 (2013.01); G01V 8/10 (2013.01); G06F 3/0416 (2013.01); G06F 3/0445 (2019.05); G16H 20/13 (2018.01); A61J 2200/70 (2013.01); G06F 2203/04102 (2013.01)

(58) Field of Classification Search
None
See application file for complete search history.

(56) References Cited

U.S. PATENT DOCUMENTS 10,437,359 B1 * 10/2019 Wang ............... G06F 3/016
2011/0037485 A1 2/2011 Kiy
(Continued)

FOREIGN PATENT DOCUMENTS

WO WO 2019/011787 A1 1/2019

OTHER PUBLICATIONS

International Search Report and Written Opinion, Patent Cooperation Treaty Application No. PCT/US2020/062707, dated Feb. 25, 2021, thirteen pages.

Primary Examiner — Nasima Monsur
(74) Attorney, Agent, or Firm — Fenwick & West LLP

(57) ABSTRACT

An object container apparatus includes a housing, a sensor sheet, and one or more computer processors coupled to the sensor sheet. The housing comprises one or more interior surfaces forming a cavity. The sensor sheet is positioned within the cavity and comprises one or more arrays of capacitive touch pads. The one or more arrays of capacitive touch pads are arranged substantially parallel to each other in order to form a space within the cavity where an object can be inserted. The one or more computer processors are coupled to the one or more arrays of capacitive touch pads and configured to process capacitance measurements derived from the one or more arrays of capacitive touch pads. The object container apparatus functions to detect an object in the space via processing of capacitance measurements by the one or more computer processors.

21 Claims, 11 Drawing Sheets

(51) Int. Cl.
    *G01V 3/12*    (2006.01)
    *G01S 15/04*   (2006.01)

(56) References Cited

U.S. PATENT DOCUMENTS

| | | | |
|---|---|---|---|
| 2013/0279769 A1* | 10/2013 | Benkley, III | G06F 3/0445 |
| | | | 382/124 |
| 2015/0302173 A1 | 10/2015 | Forster | |
| 2016/0093644 A1* | 3/2016 | Ki | H01L 27/1222 |
| | | | 257/43 |
| 2016/0132661 A1* | 5/2016 | Dixit | G16Z 99/00 |
| | | | 53/410 |
| 2016/0354283 A1* | 12/2016 | Cho | A61J 7/00 |
| 2017/0294105 A1* | 10/2017 | Mehregany | A61J 7/0436 |
| 2018/0104154 A1 | 4/2018 | Dantsker et al. | |

\* cited by examiner

250

```
┌─────────────────────────────────────────────────────────────┐
│ Receive First and Second Capacitance Measurements Derived from │
│           Capacitive Touch Pads of Sensor Sheet              │
│                            260                               │
└─────────────────────────────────────────────────────────────┘
                              │
                              ▼
┌─────────────────────────────────────────────────────────────┐
│       Process First and Second Capacitance Measurements      │
│                            270                               │
└─────────────────────────────────────────────────────────────┘
                              │
                              ▼
┌─────────────────────────────────────────────────────────────┐
│ Detect Blister Pill Pack based on Change between First and Second │
│                    Capacitance Measurements                  │
│                            280                               │
└─────────────────────────────────────────────────────────────┘
```

FIG. 2C

OBJECT-DETECTING CONTAINER APPARATUS

CROSS REFERENCE TO RELATED APPLICATIONS

This application claims the benefit of U.S. Provisional Application No. 62/942,266, filed Dec. 2, 2019, which is incorporated by reference in its entirety.

TECHNICAL FIELD

This disclosure relates generally to an object, e.g., a pill pack, container apparatus, and more particularly, to an object container apparatus comprising one or more sensor sheets.

BACKGROUND

Container apparatus technologies that include sensor components are used for monitoring objects placed contained within the container apparatuses (e.g., within a housing of the container apparatus). For example, container apparatuses for blister pill packs include various sensor components that receive sensor data indicative of user interaction with a blister pill pack, such as to ensure patients take their medication on time.

However, conventional container apparatuses are narrowly designed for detection of objects with specific characteristics, such as objects with specific dimensions. As such, the sensor components of conventional container apparatuses are unreliable for monitoring objects that have different characteristics than those for which the container apparatuses were designed (e.g., different blister pill pack dimensions or pill size). Other conventional container apparatuses are designed to address differences in object type through the inclusion of multiple sensors of different types (e.g., an accelerometer, a microphone, a capacitive sensor, etc.) or sensors that require bulky or rigid components (e.g., inductive sensors that include inductive and conductive coils and require outer casings to reduce noise interference). However, such container apparatus designs have a number of constraints, for example, they are complicated to manufacture, resource-intensive to manufacture, and cumbersome for users.

SUMMARY

An object container apparatus includes, for example, a housing, a sensor sheet, and one or more computer processors communicatively coupled to the sensor sheet. The housing comprises one or more interior surfaces forming a cavity. The sensor sheet is positioned within the cavity and comprises one or more arrays of capacitive touch pads. The one or more arrays of capacitive touch pads are arranged substantially parallel to each other in order to form a space within the cavity where an object can be inserted (e.g., a blister pill pack). The one or more computer processors are coupled to the one or more arrays of capacitive touch pads and configured to process capacitance measurements derived from one or more arrays of capacitive touch pads (e.g., derived from analog capacitance signals received by the capacitive touch pads). The object container apparatus advantageously functions to detect an object in the space via processing of capacitance measurements derived from the one or more arrays of capacitive touch pads by the one or more computer processors. The one or more computer processors may further determine the presence, absence, orientation, position, or movement (e.g., direction, velocity, etc.) of an object in the space. In an exemplary embodiment, the object container apparatus is a blister pill pack container that houses blister pill packs and functions to detect movement and the extent of the movement of the blister pill packs in or out of the blister pill pack container.

According to an embodiment, a blister pill pack container apparatus comprises a housing having a first side and a second side, the first side having a first end and a second end and the second side having a first end and a second end. The first end of the first side and the first end of the second side form an enclosed end of the housing and the second end of the first side and the second end of the second side form a closeable end of the housing. The first side has an exterior surface and an interior surface and the second side has an exterior surface and an interior surface, the exterior surface of the first side and the exterior surface of the second side forming an exterior of the housing and the interior surface of the first side and the interior surface of the second side forming a cavity, The cavity has a sensor sheet attached to the interior surface of the first side and the interior surface of the second side. The sensor sheet comprises a flexible substrate and a first and second array of capacitive touch pads positioned on the flexible substrate, the capacitive touch pads of the first and second arrays comprising one or more layers of conductive material. The flexible substrate is folded to arrange the first array of capacitive touch pads substantially parallel to the second array of capacitive touch pads with a space between the first and second array of capacitive touch pads for inserting a blister pill pack within the cavity. The cavity further having a printed circuit board (PCB) positioned between the sensor sheet and the interior surface of the first or second sides. The PCB comprises a capacitive sensor driver chip coupled with the first array and the second array of capacitive touch pads. The capacitive sensor driver chip has a terminal to receive at least first and a second capacitance signals from the first and the second array of capacitive touch pads. The PCB further comprises a microcontroller configured to process a change between the first and the second capacitance signals to detect a blister pill pack in the space.

According to one embodiment a blister pill pack apparatus, comprising a housing having one or more interior surfaces forming a cavity. The cavity has one or more sensor sheets attached to the one or more interior surfaces. The one or more sensor sheets comprise at least a first and second array of capacitive touch pads comprising one or more layers of conductive material. The one or more sensor sheets are arranged to position the first array of capacitive touch pads substantially parallel to the second array of capacitive touch pads with a space between the first and second array of capacitive touch pads for inserting a blister pill pack within the cavity. The cavity additionally has a capacitive sensor driver chip coupled with the one or more arrays of capacitive touch pads, the capacitive sensor driver chip having a terminal to receive at least a first and a second capacitance signals from the one or more arrays of capacitive touch pads. The cavity further having a microcontroller configured to process a change between the first and the second capacitance signals to detect a blister pill pack in the space.

BRIEF DESCRIPTIONS OF THE DRAWINGS

The disclosed embodiments have other advantages and features which will be more readily apparent from the following detailed description of the invention and the appended claims, when taken in conjunction with the accompanying drawings, in which:

FIG. 2C illustrates a process for detecting the blister pill pack in a blister pill pack container apparatus, according to one embodiment.

DETAILED DESCRIPTION

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein. In particular, in other embodiments that those depicted in the figures below the various components may include fewer, additional, or different components which may be configured differently than the components depicted or described.

Example Object Container Apparatus Configuration

Figure 1:
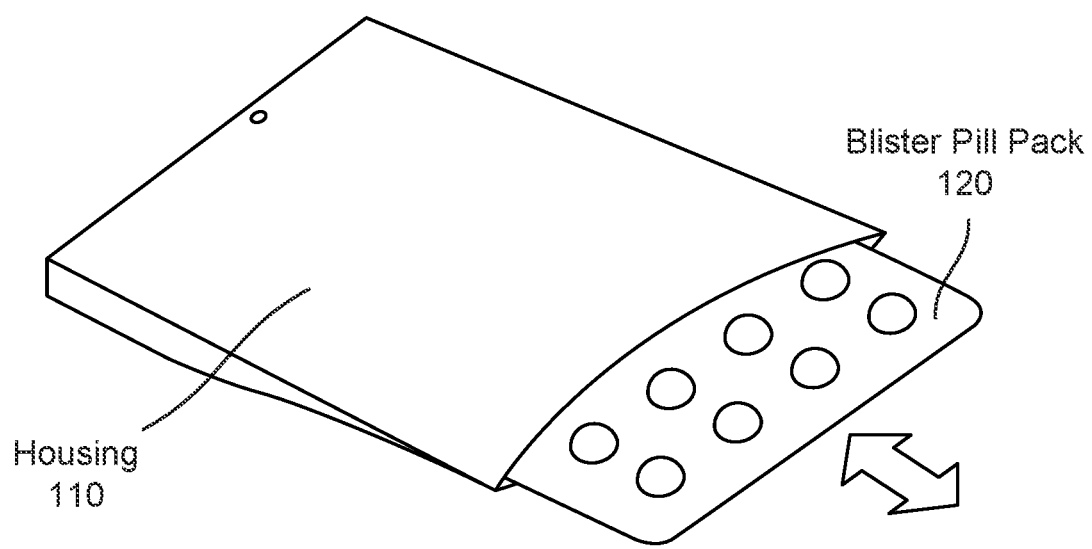
FIG. 1 illustrates a perspective view of a blister pill pack container apparatus, according to one embodiment.

FIG. 1 illustrates an embodiment of a perspective view of a blister pill pack container apparatus 100. In the embodiment shown, the blister pill pack container apparatus 100 includes a housing 110 and a blister pill pack 120. In one example embodiment, the housing 110 forms a sleeve with an enclosed end and two enclosed edges opposite each other and perpendicular to the enclosed end that form three sides of the housing. A fourth side has a closeable end that is opposite the enclosed end and is perpendicular to the two edges. A blister pill pack 120 can be inserted or removed.

As will be described in greater detail below, the housing 110 includes one or more sensor sheets and one or more computer processing components (e.g., microcontrollers). The one or more sensor sheets include sensors that receive analog signals indicative of the presence of the blister pill pack 120. The one or more computer processing components are configured to process the analog signals received by the sensors of the one or more sensor sheet in order to detect the blister pill pack 120 or otherwise determine information describing the blister pill pack 120. For example, the one or more computer processing components may be configured to detect when the blister pill pack 120 is inserted into the housing 110 or removed from the housing 110 via the closeable end.

As depicted in FIG. 1, the blister pill pack 120 is an asymmetrical structure comprising a top including a set of pills encased in plastic blisters and a bottom comprising a layer of frangible aluminum foil. The blister pill pack 120 has a base with rectangular dimensions (e.g., a three-inch width and five-inch length) and plastic blisters with a dome-like structure extending above the base (e.g., a quarter-inch height). The blister pill pack 120 can be inserted lengthwise into the housing 110 in FIG. 1, but may be inserted widthwise or otherwise in other embodiments. The blister pill pack 120 is depicted for the purposes of illustration only, and the blister pill pack container apparatus 100 may be used with blister pill packs having different characteristics). In particular, the blister pill pack container apparatus 100 can be used to house or detect any blister pill pack with dimensions that allow the blister pill pack to that fit within the housing 110. For example, other blister pill packs may have a base with larger or smaller dimensions than the blister pill pack 120, or have plastic blisters with a larger or smaller volume size (e.g., blisters of different height, width and/or length) than the blister pill pack 120). Furthermore, the blister pill pack container apparatus 100 may be used with pill packs having different structures or designs than the blister pill pack 120, such as clamshell pill packs or circular pill packs. In this case, components of the blister pill pack container apparatus 100 may be adjusted in order to house or detect the various types of pill packs, such as changing the shape or size of the housing 110 or internal components of the blister pill pack container apparatus 100 (e.g., the components discussed below with reference to FIGS. 2-4). In some embodiments, the blister pill pack container apparatus 100 is integrated into, or attachable to, other components not depicted in FIG. 1 (e.g., another apparatus or device). For example, the blister pill pack container apparatus 100 may be integrated into a mobile phone case, or attachable to a mobile phone case or a mobile phone itself via a variety of attachment methods such as magnets, adhesive or clips. Other components of the blister pill pack container apparatus 100 may be integrated with or attached to include, but are not limited to, accessories commonly carried such as wallets, purses, mirrors, and makeup cases.

Figure 2A:
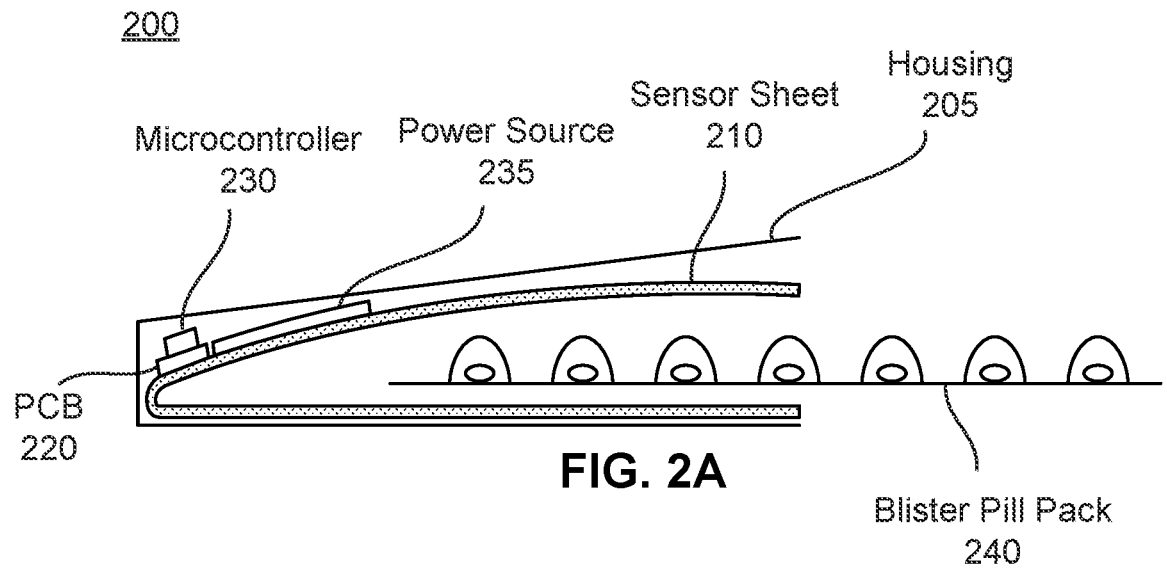
FIG. 2A illustrates a side cross-sectional view of a blister pill pack container apparatus, according to one embodiment.
Figure 2B:
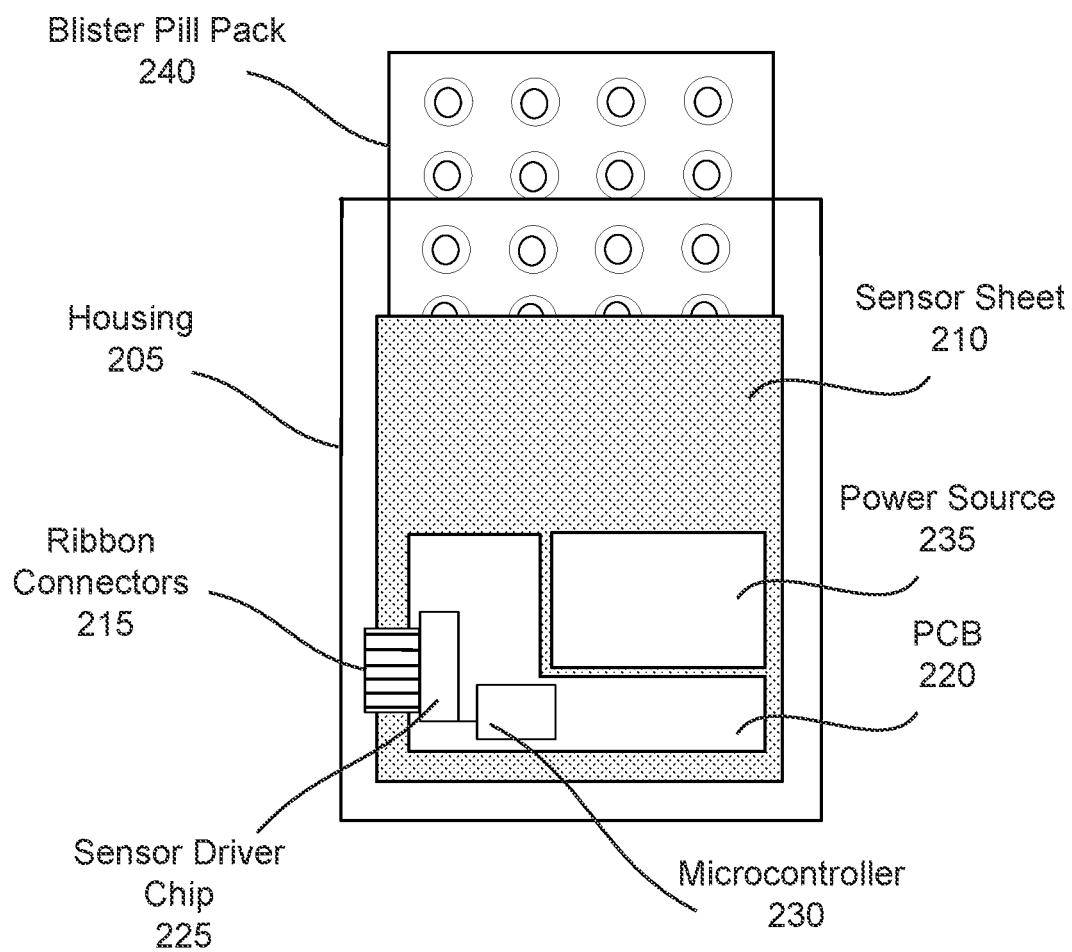
FIG. 2B illustrates a frontal cross-sectional view of the blister pill pack container apparatus depicted in FIG. 2A, according to one embodiment.

FIGS. 2A and 2B illustrate cross-sectional views of an embodiment of a blister pill pack container apparatus 200. In particular, FIG. 2A illustrates a side cross-sectional view of the blister pill pack container apparatus 200. FIG. 2B illustrates a frontal cross-sectional view of the blister pill pack container apparatus 200. The blister pill pack container apparatus 200 may be an embodiment of the blister pill pack container apparatus 100. In the embodiment shown, the blister pill pack container apparatus 200 includes a housing 205, a sensor sheet 210, a printed circuit board (PCB) 220, and a power source 235. A blister pill pack 240 is inserted into a cavity formed by the housing 205, and particularly into a space created by a folding of the sensor sheet 210, as described in greater detail below with reference to the sensor sheet 210.

The housing 205 includes a first side and a second side (e.g., a front side and a back side) structured to form a cavity that receives the blister pill pack 240. In other embodiments, the housing 205 includes additional sides (e.g., a left side, right side, bottom side, top side, etc.). The cavity of the sleeve is formed with the first and the second sides of the housing and a closed end opposite the end where the cavity opens. A closeable end is where the blister pill pack 240 is inserted into the cavity. The housing sleeve may be manufactured from various materials, such as paper, fabric, leather, faux leather, glass, or plastic, as described in greater detail below with reference to FIG. 5. In some embodiments, the blister pill pack container apparatus 200 includes a mechanism for closing the closeable end of the housing 205, such as a latch mechanism, flap, band, rotatable plastic barrier, or magnet.

In various embodiments, the components of the blister pill pack container apparatus 200 are attached to the housing 205 or other components via one or more different adhesives. For example, the components may be attached in full or part with various tapes, glues, compressible materials, baking processes, printing processes, welding processes, or other adhesives, as described in greater detail below where relevant. In one embodiment, the first and second sides of the housing are attached (e.g., at the closed or sides of the sleeve) using a sonic welding process. In the same or different embodiment, a compressible material is inserted between the sensor sheet 210 and the housing 205 to provide support to the sensor sheet 210, allowing it to conform to blister pill packs with varying heights (e.g., varying plastic blister heights).

The sensor sheet 210 is positioned within the cavity formed by the housing 205. In the embodiment shown in FIGS. 2A-B, the sensor sheet 210 is comprised of a flexible substrate layer and one or more sensors. The one or more sensors are positioned on one side of the flexible substrate layer (e.g., painted, printed, attached via adhesive, etc.). As depicted, the sensor sheet may be folded inward on the side including the conductive material (i.e., the inner side of the sensor sheet 210) in order to arrange at least a first sensor of the one or more sensors substantially parallel to a second sensor the one or more sensors. The folding of the inner side of the sensor sheet 210 further creates a space between the first and second sensors where the blister pill pack 240 is inserted. The flexible substrate layer may be manufactured from various bendable materials such as polyethylene (PE), polyethylene terephthalate (PEET), polycarbonate (PC), polyvinyl chloride (PVC), or any other suitable material. Advantageously, the flexible substrate enables the sensor sheet 210 to conform to the shape of various types of blister pill packs (e.g., for housing or detecting the various different types of blister pill packs). In one embodiment, an antioxidant layer (e.g., graphite-based ink) is applied over the conductive materials on the sensor sheet 210 in order to prevent corrosion or oxidization of the conductive material.

The sensors of the sensor sheet 210 comprise one or more layers of conductive material forming one or more arrays of capacitive touch pads. The conductive material can include various materials capable of receiving analog capacitance signals, such as silver-based conductive paint, carbon-based conductive paint, copper tape, conductive graphite inks, or some combination thereof. The capacitive touch pads receive analog capacitance signals via the conductive material that describe a mutual capacitance of space around the sensor sheet 210. In particular, the capacitive touch pads receive analog capacitive signals indicative of changes to the mutual capacitance resulting from contact with the blister pill pack 240 or resulting from close proximity of the blister pill pack 240 (e.g., within one to five millimeters). The shape, arrangement, and number of capacitive touch pads positioned on the flexible substrate layer can vary depending on the particular embodiment. In particular, the shape, arrangement, and number of capacitive touch pads may be specifically designed to mitigate false positive results by arranging the capacitive touch pads to produce a distinctive sequence of capacitance signals indicative of a blister pill pack sliding across the capacitive touch pads. Furthermore, the structural composition of the conductive material for each individual capacitive touch pad can vary depending on embodiment, such as a solid fill or grid pattern, etc. In other embodiments than that depicted in FIGS. 2A and 2B, the sensors of the sensor sheet 210 or another component of the blister pill pack container apparatus 200 can additionally, or alternatively, include one or more of various other types of sensors, such as inductive sensor pads, resistive tactile sensors, infrared (IR) sensors, piezolelectric sensors, audio sensors, micro-electromechanical systems (MEMS) sensors, weight sensors, temperature sensors, hall-effect sensors, or acceleration sensors. Various embodiments including other types of sensors are described in greater detail below, e.g., in reference to FIGS. 3A-G.

In some embodiments, the blister pill pack container apparatus 200 includes a ground plane layer that shields the one or more capacitive touch pads on the inner side of the sensor sheet 210 from ambient electromagnetic noise or other electromagnetic interference. In particular, the ground plane layer may be positioned between the outwardly folded side of the sensor sheet 210 (i.e., the outer side of the sensor sheet 210) and the interior surfaces of the first or second sides of the housing 205. In some cases, the ground plane layer is connected directly to the sensor sheet 210, such as foldable extensions on one or both ends of the sensor sheet 210 that can be folded back over the outer side of the sensor sheet 210, as described in greater detail below with reference to FIG. 3B. Like the one or more arrays of capacitive touch pads, the ground plane layer comprises one or more layers of conductive material (e.g., conductive paints or other materials) capable of reducing interference by means of electromagnetic shielding. Additionally, or alternatively, the one or more layers of conductive material may be capable of leveling a floating ground voltage of a circuit of the blister pill pack container apparatus 200 (e.g., an integrated circuit (IC) of the PCB 220, as described below) with that of earth ground voltage via capacitive coupling of the blister pill pack 240 and a user of the blister pill pack container apparatus 200 (e.g., through holding the blister pill pack container apparatus 200). Furthermore, capacitance measurements derived from the conductive material of the ground layer may be processed by the microcontoroller 230 to reduce noise (e.g., using the capacitance measurements as a reference), as described in greater detail below. The conductive material of the ground plane layer may be printed or otherwise affixed to a flexible substrate, such as the flexible substrate of the sensor sheet 210. The ground plane layer and the one or more arrays of capacitive touch pads may be separated by a dielectric separator layer comprised of one or more dielectric materials, such as ethylene vinyl acetate (EVA) tape or other relevant dielectrics. The dielectric separator layer may be overlaid on the inner or outer side of the sensor sheet 210, the ground plane layer, or both (e.g., via adhesives) Alternatively, the ground plane layer may include the separator layer, where the one or more layers of conductive material of the ground plane layer are printed or painted on the separator layer. The separator layer can prevent too much electrical coupling between the arrays of capacitive touch pads and the ground plane layers which might reduce the sensitivity of the arrays of capacitive touch pads. Further, the dielectric separator layer can minimize power consumption (e.g., from the power source 235) when the sensor sheet is active. The dielectric separator additionally ensures uniform distance between the ground plane layers and the capacitive touch pads. Embodiments of a sensor sheet that include a ground plane layer is described in greater detail below with reference to FIGS. 3B-C.

In some embodiments, the sensor sheet 210 includes an insulation layer applied over the one or more layers of conductive material on the inner side of the sensor sheet 210 relative to the fold. The insulation layer insulates the one or more arrays of capacitive touch pads formed by the conductive material from electromagnetic noise or humidity. Like the separator layer described above with reference to the ground plane layer, the insulation layer may be comprised of ethylene-vinyl acetate (EVA), or may be comprised of other insulating materials such as various acrylic foam tapes (e.g., 3M™ VHB™ tapes).

In some embodiments the sensor sheet 210 is arranged within the housing 205 differently than depicted in FIGS. 2A and 2B. In one embodiment, the sensor sheet 210 is not folded and includes one or more layers of conductive material or other materials described herein. In this case, the sensor sheet 210 may be attached to either the first or second side of the housing 205 such that the side of the sensor sheet 210 that includes the conductive material faces inward towards the opposing side of the housing 205. As such, the blister pill pack 240 can be inserted between the conductive material of the sensor sheet 210 and the opposing side of the housing 205. In an alternative embodiment, the sensor sheet 210 is comprised of first and second separate sensor sheets that are positioned within the housing 205 in order to arrange one or more arrays of capacitive touch pads of the first sensor sheet substantially parallel to the second sensor sheet, similarly to the embodiment depicted in FIGS. 2A and 2B.

In the same or different embodiments, the sensor sheet 210 includes a PCB fully or partially in place of the flexible substrate (e.g., the PCB 220). In this case, some or all of the conductive material may be etched on the PCB of the sensor sheet 210. The PCB of the sensor sheet 210 may be rigid or may alternatively be made from flexible PCB material (e.g., flex PCB). Sensor sheet embodiments including a PCB are described in greater detail below with reference to FIG. 4B.

The sensor sheet 210 and the PCB 220 are communicatively coupled via one or more ribbon connectors 215 (e.g., including flexible conductive traces). The one or more ribbon connectors 215 are attached at a first end to a respective capacitive touch pad of the one or more arrays of capacitive touch pads and attached at a second end to an input port of a sensor driver chip 225 component of the PCB 220. The ribbon connectors 215 transmit capacitance signals received by the one or more set of capacitive touch pads of the sensor sheet 210 to the sensor driver chip 225. In one embodiment, the ribbon connectors 215 are connected to a flexible printed circuit (FPC) connector component of the PCB 220 (e.g., an FPC connector soldered to the PCB 220). In an alternative embodiment, the ribbon connectors 215 are attached directly to the PCB 220 (e.g., soldered directly to the PCB 220). In the same or different embodiments, the ribbon connectors 215 are attached directly to the flexible substrate of the sensor sheet 210 (e.g., via heat pressing, soldering, or adhesive). It should be understood by those skilled in the art that in alternative embodiments to that depicted in FIB. 2 other types of electrical connectors than ribbon connectors may be used.

The PCB 220 comprises an IC including the sensor driver chip 225 and a microcontroller 230. Electrical traces connecting the components of the IC may be positioned in order to minimize interference either from trace cross talking or from sources of external electrical noise. The sensor driver chip 225 comprises a set of terminals (e.g., input or output ports) connected to one end of the ribbon connector of the ribbon connectors 215. As depicted, the PCB 220 is positioned between the interior surface of the first side of the housing 205 and the sensor sheet 210. The PCB 220 may be affixed to the housing 205, the sensor sheet 210, or both, using adhesive. In the case where the housing 205 is made with injection molded plastic, the PCB 220 may be fixed to the housing 205 using various fasteners (e.g., screws or bolts) In alternative embodiments, the PCB 220 may be positioned at a different location in the blister pill pack container apparatus 200, such as between the interior surface of the second side of the housing 205 and the sensor sheet 200, on the exterior surface of the first or second side of the housing 205, in the space created by the fold of the sensor sheet 210, or as an integrated component of the sensor sheet 210 or housing 205.

The sensor driver chip 225 processes analog capacitance signals received from the capacitive touch pads, such as converting analog capacitance signals to capacitance measurement values that can be provided to other components of the PCB 220 (e.g., the microcontroller 230). The sensor driver chip 225 may include driver software configured to process capacitance signals, and may additionally, or alternatively, include other driver software configured to process other types of signals from other types of sensors (e.g., temperature or the various types of sensors discussed above with reference to the sensor sheet 210). The sensor driver chip 225 may have a polling frequency at which analog capacitance signals are received from the capacitive touch pads on a continual or periodic basis. The polling frequency of the sensor driver chip 225 may be controlled by another component of the PCB 220 (e.g., the microcontroller 230). In some embodiments, the sensor driver chip 225 is an integrated component of the microcontroller 230.

The microcontroller 230 controls components of the PCB 220. In particular, the microcontroller 230 processes capacitance measurements received from the sensor driver chip 225 (e.g., capacitance values derived from analog capacitance signals). In some embodiments, the microcontroller 230 includes firmware configured to process capacitance measurements in order to determine information describing the blister pill pack 240 in the space between the first and second arrays of capacitive touch pads, as described below with reference to FIG. 2C. In particular, the microcontroller 230 can detect changes in the mutual capacitance of the space created by the fold of the sensor sheet 210 indicative of the presence of the blister pill pack 240, such as a change that surpasses a specific threshold or reference level. Additionally, or alternatively, the firmware of the microcontroller 230 may be configured to determine a movement direction, movement speed, position, extent, or orientation of the blister pill pack 240 using capacitance measurements received from the sensor driver chip 225. The firmware of the microcontroller 230 may be additionally, or alternatively, configured to process other signals received from other sensors (e.g., other sensors of the sensor sheet 210) in order to determine information relating to a blister pill pack detection. The firmware of the microcontroller 230 may be further configured to filter out false positives and reduce noise using various logic and algorithms. For example, the firmware of the microcontroller 230 may process capacitance measurements and a reference capacitance measurement (e.g., derived from a ground plane layer) received from one or more capacitive touch pads, such as to account for ambient electrical noise. As another example, the firmware of the microcontroller 230 may be configured to use one or more algorithms to reduce electrical noise without using a reference capacitance measurement (e.g., when no ground layer is present, as depicted in FIGS. 2A-B). The microcontroller 230 may store information associated with a detection of the blister pill pack 240, such as a time of the detection, a measured change in capacitance associated with the detection, or related information describing the blister pill pack 240. In other embodiments than that depicted in FIGS. 2A-B, one or more different computer processors (or processing systems, e.g., controllers, state machines, application specific integrated circuits, field programmable gate arrays) may be used to control the components of the blister pill pack container apparatus 200. Furthermore, the one or more different computer processors may be components of one or more different electronic circuits than the IC of the PCB 220. For instance, the sensor sheet 210 may be coupled to a multi-chip central processing unit (CPU). In this case, the CPU may be positioned within the housing 205 or may be positioned externally (e.g., on the exterior of the housing 205 or separately from the blister pill pack container apparatus 200).

In some embodiments, the firmware of the microcontroller 230 may be configured to avoid storing redundant information, such as only logging a blister pill pack detection when the information associated with the detection indicates that the blister pill pack 240 was inserted into the space or removed from the space, but not both. Furthermore, the firmware of the microcontroller 230 may be configured to control respective functions of various other components of the blister pill pack container apparatus 200, such as keeping an accurate timer and minimizing power consumption of the power source 235.

As described above with reference to the blister pill pack 120, the blister pill pack 240 inserted may be comprised of a top side including a set of pills and corresponding plastic blisters and a bottom side including frangible aluminum foil. As such, the bottom side of the blister pill pack 240 is closer to one or more arrays of capacitive touch pads on an adjacent side of the space side than one or more arrays of capacitive touch pads on the opposite side of the space. As aluminum foil is more conductive than the pills or plastic blisters, the analog capacitance measurements derived from the closer one or more arrays of capacitive touch pads are more indicative of the blister pill pack than capacitance measurements derived from the further one or more arrays of capacitive touch pads. As such, the folding of the sensor pack 220 advantageously enables the microcontroller 230 to detect the blister pill pack 240 regardless of the orientation of the blister pill pack 240. As a further advantage, the microcontroller 230 can determine the orientation of the blister pill pack 240 based at least in part on a discrepancy between capacitance measurements derived from the closer one or more arrays of capacitive touch pads and derived from the further one or more arrays of capacitive touch pads.

In some embodiments, the firmware of the microcontroller 230 is configured to detect the presence or absence of individual pills in the blister pill pack 240. As an example, the first or second arrays of capacitive touch pads of the sensor sheet 210 may be configured to provide capacitance measurements localized to individual blisters of the blister pill pack 240, or more generally, the location of individual pills within various pill packs. For instance, individual capacitive touch pads of the arrays of capacitive touch pads may be roughly equal to or smaller than the size of individual blisters of the blister pill pack 240 or arranged similarly to the blisters of the blister pill pack 240. In this case, the capacitance measurements derived from the individual capacitive touch pads may be precise enough for the microcontroller 230 to identify discrepancies resulting from perforation of the frangible aluminum layer. Additionally, or alternatively, the capacitance measurements derived from the individual capacitive touch pads, may be precise enough for the microcontroller 230 to identify discrepancies resulting from the presence of absence of individual pills within the plastic blisters. In this case, the discrepancies between capacitance measurements identified by the microcontroller 230 may be on the order of picofarads. Furthermore, to facilitate detection of the presence or absence of individual pills, the firmware of the microcontroller 230 may be configured to perform various algorithms for filtering received capacitance measurements to identify such precise discrepancies. An embodiment of a sensor sheet configured for detection of individual pills is further described below with reference to FIG. 3A.

In some embodiments, the PCB 220 includes one or more components enabling the microcontroller 230 to communicate with an external computing device (e.g., a mobile phone, a desktop computer, a laptop computer, a remote server computer, etc.). For instance, the PCB 220 may include various wireless communication modules, such as a WiFi module, a Bluetooth module, a near-field communication (NFC) module, a ZigBee module, or any other suitable wireless communication protocol. As another example, the PCB 220 may include various terminals enabling wired communication with an external computing device, such as a universal serial bus (USB) port.

In the same or different embodiments, the microcontroller 230 communicates with an application associated with the blister pill pack apparatus 220, such as a mobile or web application on an external computing device. In this case, the microcontroller 230 may provide information relating to a detection of the blister pill pack 240 to the application, such as to log when a user of the blister pill pack container apparatus 200 removes or inserts the blister pill pack 240 into the blister pill pack container apparatus 200, indicating the user may have taken medication in the blister pill pack. The microcontroller 230 may further provide capacitance measurements or other information to an external computing device for further processing (e.g., processing that utilizes additional computing resources of the external computing device). In some cases, operation of the microcontroller 230 may be configured via the application, such as to configure how the microcontroller 230 processes capacitance measurements or other measurements derived from other sensors.

In some cases, the firmware of the microcontroller 230 is configured to communicate with the sensor driver chip 220 to adjust the sensitivity or various other settings of the one or more arrays of capacitive touch pads of the sensor sheet 210. For example, techniques like adjacent key suppression (AKS™) can be applied in the sensor driver chip 225 to in order to select an input port of the sensor driver chip 225 to use for signal processing at a particular time based on the highest magnitude of capacitance signals received from a group of input ports (e.g., input ports connected to adjacent capacitive touch pads on the sensor sheet 210). The sensor driver chip 225 may further include a guard input port that can be used to filter out false positives.

In some embodiments, the microcontroller 230 controls a user interface of the blister pill pack container apparatus 200. In one embodiment, the user interface comprises one or more Light-Emitting Diodes (LEDs) that display different colored light to convey a state of the blister pill pack apparatus 200. For example, the LEDs may display light of a first color to indicate that the blister pill pack 240 is currently inserted into the blister pill pack container apparatus 200 (e.g., a green light) and display a second color to indicate that a blister pill pack is not currently inserted into the blister pill pack container apparatus 200 (e.g., a red light). As such, the LEDs may provide user feedback to convey whether or not a user of the blister pill pack container apparatus 200 has correctly inserted the blister pill pack 240 (e.g., inserted all the way into the space between the first and second arrays of capacitive touch pads of the sensor sheet 210). The LEDs may be connected to the PCB 220 via a wired connection or may be integrated components of the PCB 220.

In example embodiments, the user interface of the blister pill pack container 200 apparatus includes other components or features, such as a digital display (e.g., on the exterior surfaces of the housing 205). For example, the user interface may include a haptic feedback component (e.g., a vibration motor or actuation component), such as a haptic component that vibrates after a user slides in the blister pill pack 240). In the same or different embodiment, the user interface includes an audio feedback component (e.g., a buzzer) such as an audio feedback component that produces a sound to remind a user of the blister pill pack container apparatus 200 to take their medications at an appropriate time. In the same or different embodiments, the user interface of the blister pill pack container apparatus 200 includes a digital interface displayed on an external computing device, such as a mobile phone, that is in communication with the blister pill pack container apparatus 200 (e.g., via the microcontroller 230).

The power source 235 is a device configured to provide power to the PCB 220 and electrical components of the blister pill pack apparatus 200 controlled by the PCB 220. For example, the power source 235 may be a rechargeable battery or battery pack, coin cells, or super capacitors. As depicted, the power source 235 is positioned next to the PCB 220, between the interior surface of the first side of the housing 205 and the sensor sheet 210. In alternative embodiments, the power source 235 may be positioned at a different location in the blister pill pack container apparatus 200, such as in one of the alternative positions described above with reference to the PCB 220.

In alternative embodiments than that depicted in FIGS. 2A-B, the blister pill pack container apparatus 200 includes one or more acceleration sensors (e.g., a gyroscope or accelerometer), as described above with reference to the sensor sheet 210. The one or more acceleration sensors may be positioned in various locations, such as on the PCB 220, the sensor sheet 210 (e.g., as an integrated component of the sensor sheet 210), along one or both of the exterior or interior surfaces of the housing 205 or on the outer side of the sensor sheet 210 (e.g., via adhesive).

The one or more acceleration sensors may be communicatively coupled to the microcontroller 230 or other components of the PCB 220, e.g., via one or more ribbon connectors or other connective wires, digitally controlled through dedicated communication channels (e.g., digital I/O ports or a serial communication bus, e.g., using the I2C, serial peripheral interface (SPI), or I2S protocols). In one embodiment, acceleration measurement received by the microcontroller 230 derived from the one or more acceleration sensors are processed in combination with capacitance measurement derived from one or more arrays of capacitive touch pads. For instance, by processing the acceleration measurements, the microcontroller 230 can determine whether a user is inserting the blister pill pack 240 into the blister pill pack container apparatus 210, e.g., based on detection of a particular orientation, movement, or vibration pattern.

In the same or different embodiment, the microcontroller 230 or one or more other sensors (e.g., the one or more arrays of capacitive touch pads) are put in a higher power-consuming state (e.g., activated) based on acceleration measurements derived from the one or more acceleration sensors, such as if the blister pill pack container apparatus is moving. Similarly, the microcontroller 230 or one or more other sensors (e.g., the one or more arrays of capacitive touch pads) are put in a lower power-consuming state (e.g., deactivated completely or put in sleep mode) based on acceleration measurements derived from the one or more acceleration sensors, such as if the blister pill pack container apparatus is not moving. As such, the one or more acceleration sensors can advantageously enable the blister pill pack container apparatus 200 to conserve power provided by the power source 235. To better achieve this result, the particular one or more acceleration sensors used as components of the blister pill pack container apparatus 200 may consume less power than the sensor sheet 210 or the PCB 220. As another example, the microcontroller 230 may process the acceleration measurements to determine specific movement of the blister pill pack container apparatus 200 (e.g. tapping, rotating, falling, etc.) to trigger specific processes (e.g., configuring the blister pill pack container apparatus 200 to function as an alarm clock after placed vertically or outputting an indication, such as a sound, that the case is free falling).

In alternative embodiments than that depicted in FIGS. 2A-B, the blister pill pack container apparatus 200 includes one or more hall-effect sensors, as described above with reference to the sensor sheet 210. The one or more hall-effect sensors may be positioned in various locations, such as described above with reference to the one or more acceleration sensors. The one or more hall-effect sensors may be communicatively coupled to the microcontroller 230 or other components of the PCB 220, e.g., via one or more ribbon connectors or other connective wires. The one or more hall-effect sensors may receive analog magnetic field signals produced by one or more magnets positioned within the housing 205 or at or near the closable end of the housing (e.g., within one or two centimeters of the closeable end). For example, the one or more magnets may also be positioned along one or both of the interior surfaces of the housing 205 (e.g., via adhesive). In this case, the microcontroller 230 may identify a change in the magnetic field due to the blister pill pack 240, such as when the blister pill pack 240 is inserted or removed from the space created by the fold of the sensor sheet 210. In one embodiment, magnetic field measurements derived from the one or more hall-effect sensors are processed by the microcontroller 230 in combination with capacitance measurements derived from one or more arrays of capacitive touch pads. In the same or different embodiment, the microcontroller 230 uses magnetic field measurements derived from the one or more hall sensors to make an initial detection of the blister pill pack 240. In the same or different embodiment, the microcontroller 230 processes magnetic field measurements derived from the one or more hall-effect sensors in combination with capacitance measurements derives from one or more arrays of capacitive touch pads. For instance, after making an initial detection using the one or more hall effect sensors, the microcontroller 230 may process capacitance measurements to determine information describing the blister pill pack 240 (e.g., movement direction, movement speed, orientation, position, extent, etc.), as described above with reference to the microcontroller 230. In some cases, the microcontroller 230 may activate the one or more arrays of capacitive touch pads after an initial detection is made. In doing so, blister pill pack container apparatus 200 may conserve power provided by the power source 235, similarly to the embodiments including an acceleration sensor described above.

In an embodiment where the closable end of the housing 205 includes a magnet (e.g., a magnet contained within a flap connected to the closeable end), the microcontroller 230 can detect an opening or closing of the closable end via the magnet based on changes in the magnetic field determined from magnetic field measurements derived from the hall-effect sensor. The microcontroller 230 may further deactivate or otherwise configure various components of the blister pill pack container apparatus 200 in order to reduce power consumption after determining the closeable end is closed. Similarly, the microcontroller 230 may activate some or all of the same or different components after determining the closeable end is opened.

In alternative embodiments than that depicted in FIGS. 2A-B, the blister pill pack container apparatus 200 includes one or more sound sensors, as described above with reference to the sensor sheet 210. The one or more sound sensors may be positioned in various locations, such as described above with reference to the one or more acceleration sensors. The one or more sound sensors may be communicatively coupled to the microcontroller 230 or other components of the PCB 220, e.g., via one or more ribbon connectors or other connective wires. The one or more sound sensors may transmit one or more sound waves, e.g., into the cavity of the housing 205. In this case, the one or more sound sensors may receive analog sound wave signals reflected back to the one or more sensors. For instance, the one or more sound sensors may include an audio emitter that outputs sound wave signals and an audio receiver that receives sound wave signals. In this case, the microcontroller 230 may compare the output sound wave signals to the received sound wave signals to determine whether the sound waves reflected off of the blister pill pack 240. In some embodiments, the microcontroller 230 may use the one or more sound sensors in combination with one or more other sensors, as described above with reference to the one or more hall-effect sensors.

In alternative embodiments than that depicted in FIGS. 2A-B, the blister pill pack detection apparatus includes one or more IR sensors, as described above with reference to the sensor sheet 210. The one or more IR sensors may be positioned in various locations, such as described above with reference to the one or more acceleration sensors. The one or more IR sensors may be communicatively coupled to the microcontroller 230 or other components of the PCB 220, e.g., via one or more ribbon connectors or other connective wires. In one embodiment, the IR sensors are positioned at or in close proximity to the closeable end of the housing 205. In the same or different embodiment, one or more arrays of capacitive touch pads (e.g., of the sensor sheet 210) are additionally positioned closer to the enclosed end of the housing 205 than the one or more IR sensors. For example, the IR sensors may be positioned between the folded ends of the sensor sheet 210 and the closeable end of the housing 205 as depicted in FIGS. 2A-B. In this case, the one or more IR sensors may receive analog IR signals describing a region at or in close proximity to the closeable end of the housing 205. The microcontroller 230 may process the IR measurements derived from the one or more IR sensors in order to make an initial detection of the blister pill pack 240, as described above with reference to the one or more hall-effect sensors.

In alternative embodiments than that depicted in FIGS. 2A-B, the blister pill pack detection apparatus includes one or more resistive sensors, as described above with reference to the sensor sheet 210. The one or more resistive sensors may be positioned in various locations, such as described above with reference to the one or more acceleration sensors. The one or more resistive sensors may be communicatively coupled to the microcontroller 230 or other components of the PCB 220, e.g., via one or more ribbon connectors or other connective wires. In one embodiment, the one or more resistive sensors are resistive switches comprising one or more transmitter terminals or receiver terminals. The one or more transmitter terminals may be coupled to a voltage high or ground. Similarly, the one or more receiver terminals may be connected to ports of the microcontroller 230 (e.g., via a pull-up or pull-down resister component of the integrated circuit of the PCB 220). The one or more resistive sensors may be comprised of copper tape and PET sheets distinct from the sensor sheet 210. Alternatively, the one or more resistive sensors may be comprised of conductive material printed on or otherwise attached directly to one or more layers of the sensor sheet 210. The microcontroller 230 may process changes in the switch state of the one or more resistive sensors, such as in order to make an initial detection of the blister pill pack 240, as described above with reference to the one or more hall-effect sensors.

FIG. 2C illustrates an embodiment of a process 250 for detecting the blister pill pack 240 in the blister pill pack container apparatus 200. In the embodiment shown, the process is performed by the microcontroller 230. In other embodiments, the process 250 may be performed by other components of the blister pill pack container apparatus 240 or an external computing device.

The process 250 begins with the microcontroller 230 receiving 260 first and second capacitance measurements from the sensor driver chip 225 derived from the capacitive touch pads of the sensor sheet 210. For example, the sensor driver chip 225 may receive a first analog capacitance signal at a first time and a second analog capacitance signal at a second time after the first time. The sensor driver chip 225 may further convert the analog capacitance signals to capacitance measurement values and provide the capacitance measurement values to the microcontroller 230. The microcontroller 230 processes 270 the first and second capacitance measurements. For instance, the microcontroller 230 may compare the first and second capacitance measurements to determine whether a change between the first and second capacitance measurement is above a threshold. From the processing, the microcontroller 230 detects 280 a blister pill pack based on a change between the first and second capacitance measurements. In particular, the microcontroller 230 may detect the change in capacitance due to the presence of the blister pill back in the space between the substantially parallel arrays of capacitive touch pads of the sensor sheet 210. The processing may be performed by the microcontroller 230 to specifically determine a movement direction, movement speed, movement extent, position, or orientation of the detected blister pill pack using the first and second capacitance measurements. In various embodiments, the microcontroller 230 may perform additional processing to detect the blister pill pack, such as comparing capacitance measurements derived from an array of capacitive touch pads on one side of the space to capacitance measurements derived from an array of capacitive touch pads on the other side.

Although FIGS. 1-2 and related description herein describe an object container apparatus for housing a blister pill pack, this is done for the purposes of illustration only and one skilled in the art will appreciate that other object container apparatuses including similar components can be used for other types of objects. Generally, an object container apparatus including a sensor sheet similar to those described herein (e.g., the sensor sheet 220) can be used to house any object involving close proximity (e.g., within one to five millimeters) or full contact between an object and the sensor. For instance, a similar object container apparatus can be used to house credit cards or paper money (e.g., functioning as a wallet), where the credit cards or paper money are inserted between two substantially parallel arrays of capacitive touch pads as depicted in FIG. 2A. Furthermore, similar techniques can be applied in other contexts than containers, such as any apparatus that includes a flexible sensor sheet as described herein. For example, similar sensor sheets as those described herein can function as a component of a flexible smart watch wrist band, a flexible touch display, a car wheel with an interface for adjusting various car settings, etc. In these cases, the sensors of the flexible sensor sheet can be used to control the associated apparatus (e.g., to receive user touch input).

Exemplary Sensor Sheet Embodiments

Figure 3A:
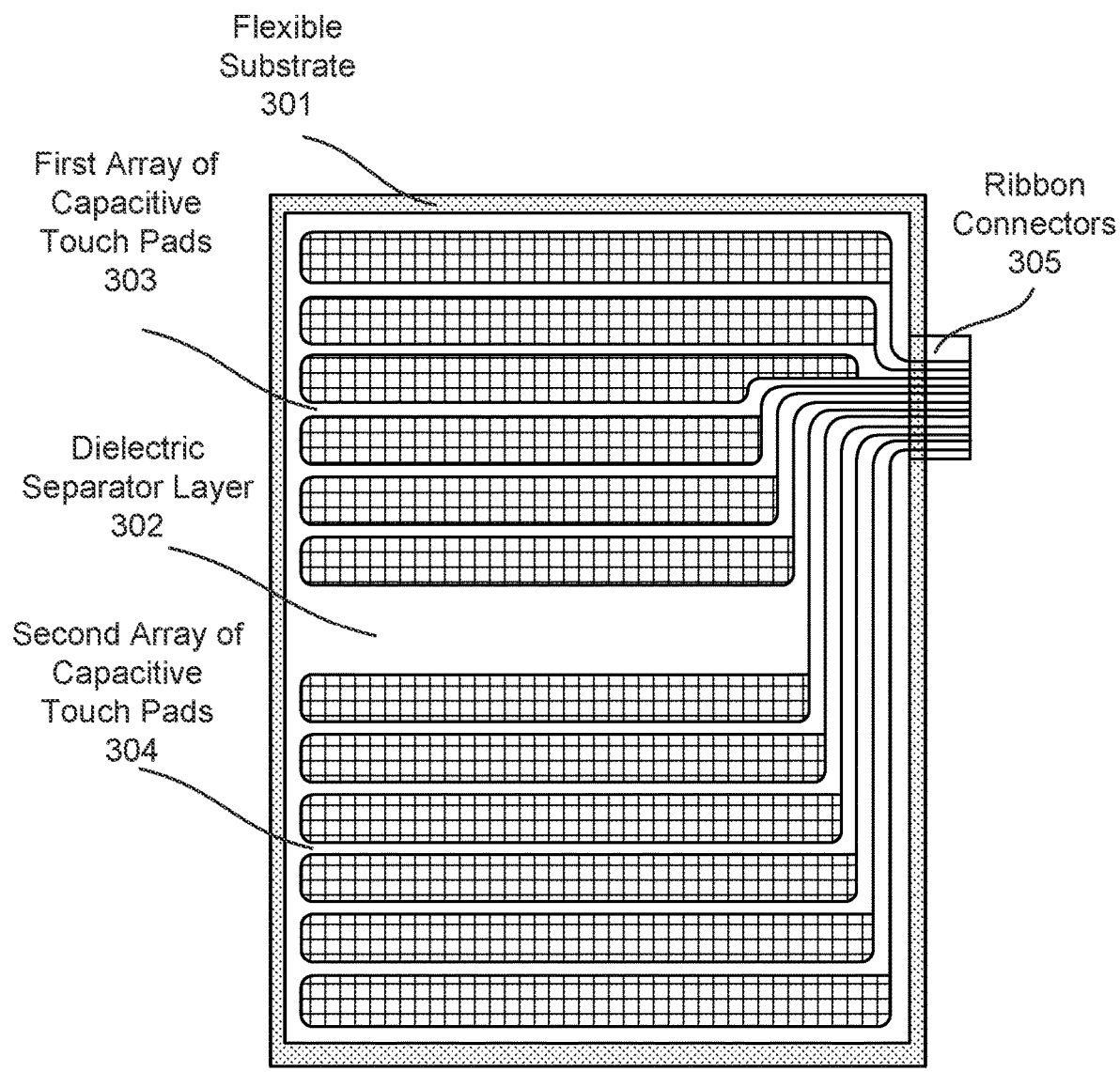
FIG. 3A illustrates a sensor sheet including a flexible substrate, a dielectric separator layer, first and second arrays of capacitive touch pads, and ribbon connectors, according to one embodiment.

FIGS. 3A-G illustrate various embodiments of sensor sheets (e.g., the sensor sheet 210). The distinctions between the sensor sheets depicted in FIGS. 3A-G are intended for the purposes of illustration only, and other sensor sheets can be used with an object container apparatus or other apparatus. One skilled in the art will appreciate that other sensor sheet embodiments can combine features from different sensor sheets depicted in FIGS. 3A-G or can include different features FIG. 3A illustrates an embodiment of a sensor sheet 300 including a flexible substrate 301, a dielectric separator layer 302, first 303 and second 304 arrays of capacitive touch pads, and ribbon connectors 305. In the embodiment shown, the dielectric separator layer 302 is overlaid on top of the flexible substrate 301. Similarly, the first 303 and second 304 arrays of capacitive touch pads are overlaid on the dielectric separator layer 302. In particular, the first 303 and second 304 arrays of capacitive touch pads are separated by a gap in the middle of the flexible substrate 301 where the sensor sheet 300 can be folded in order to arrange the first 303 and second 304 arrays of capacitive touch pads substantially parallel to each other.

As depicted, the first 303 and second 304 arrays of capacitive touch pads are comprised of, but not limited to, six capacitive touch pads. Each of the six capacitive touch pads of the first 303 and second 304 arrays are comprised of a horizontal strip of conductive material structured in a grid (e.g., mesh) pattern. The capacitive touch pads of the first 303 and second 304 arrays are connected to respective conductive traces of the ribbon connectors 305, which can be connected to a capacitive sensor chip driver of a PCB (e.g., the sensor driver chip 225). In other embodiments than that depicted in FIG. 3A, the first 303 or second 304 arrays may include more or less capacitive touch pads, or include one or more of capacitive touch pads comprised of conductive material arranged differently (e.g., in vertical strips) or structured using various other patterns (e.g., a solid fill pill).

In an alternative embodiment to that depicted in FIG. 3A, the first or second arrays of capacitive touch pads are comprised of a higher number of smaller portions of conductive material (e.g., a grid of squares of conductive material). For example, the strips of conductive material depicted in FIG. 3A may instead be divided into uniform squares of conductive material. As such, some or all of the capacitive touch pads may be closer in size to the individual pills in a blister pill pack container. In this case, a microcontroller (e.g., the microcontroller 230) receiving capacitance measurements derived from the first or second arrays of capacitive touch pads may be configured to process the capacitance measurements to detect the presence or absence of pills in a pill pack container, as described above with reference to the microcontroller 230.

Figure 3B:
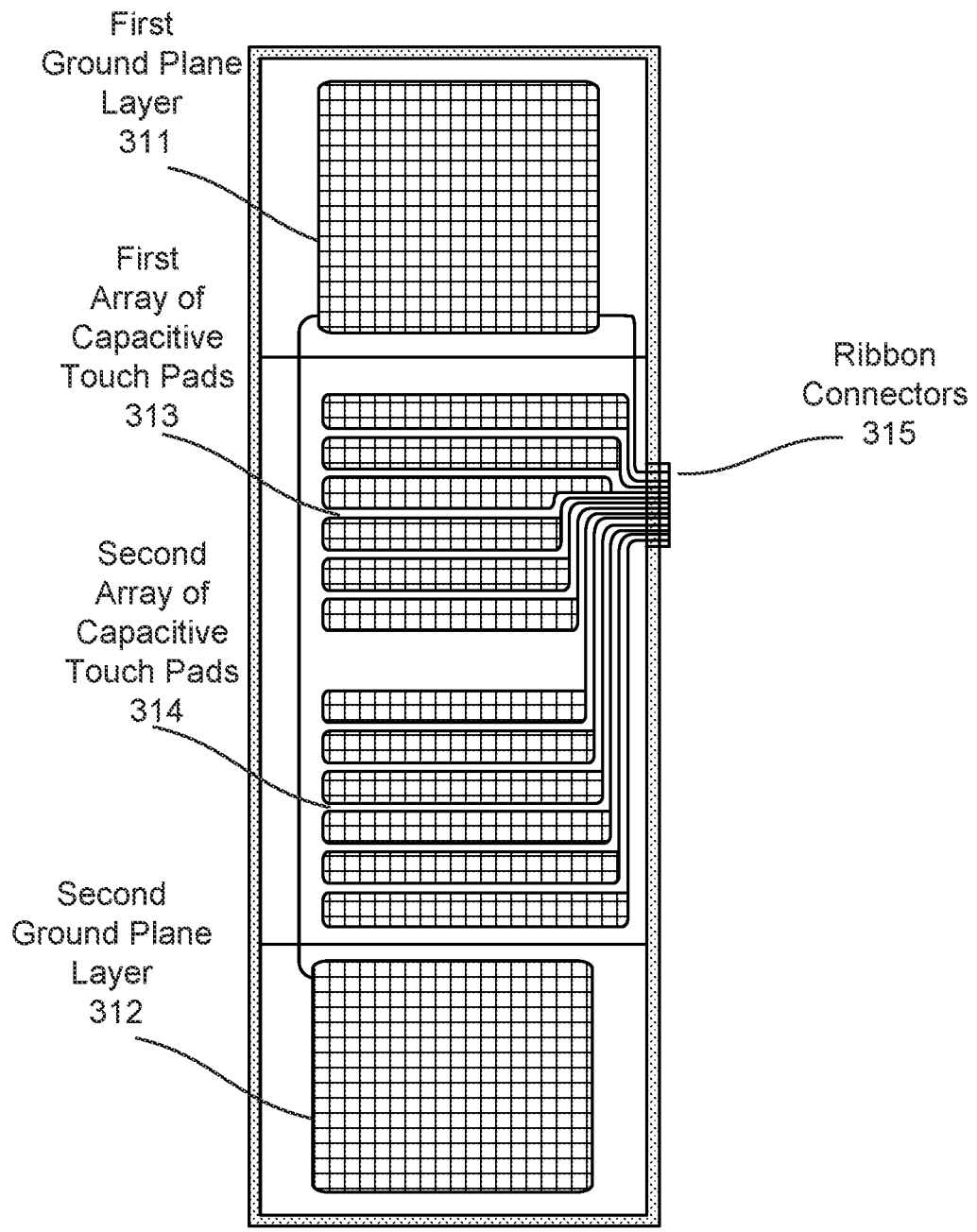
FIG. 3B illustrates a top-down view of a sensor sheet including a first ground plane layer and a second ground plane layer, according to one embodiment.
Figure 3C:
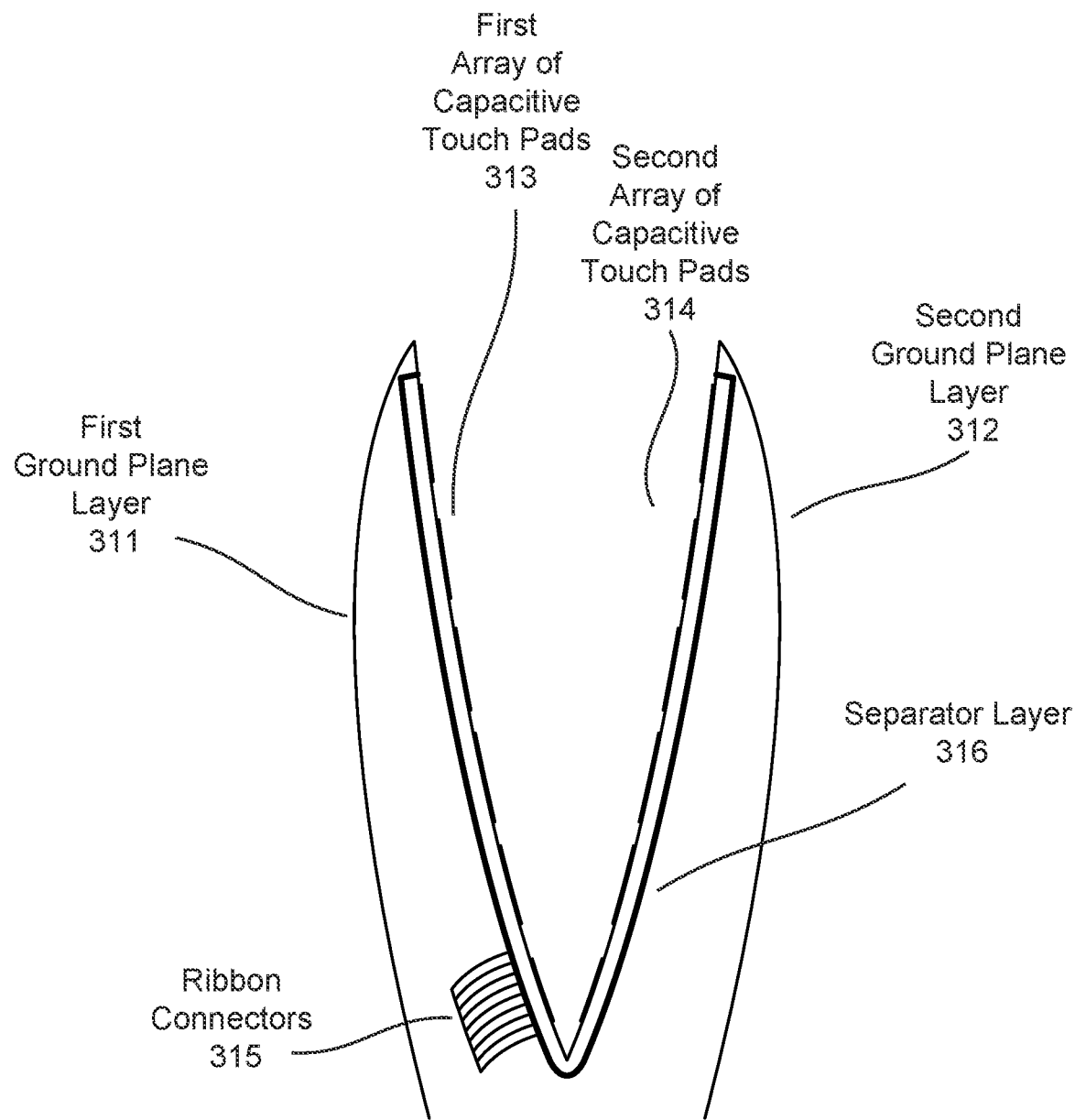
FIG. 3C illustrates a side view of the sensor sheet depicted in FIG. 3C including folding of the first ground plane player and the second ground plane layer, according to one embodiment.

FIGS. 3B-C illustrate an embodiment of the sensor sheet 310. In particular, FIG. 3B illustrates a top-down view of the sensor sheet 310 including the first ground plane layer 311 and the second ground plane layer 312. FIG. 3C illustrates a side view of the sensor sheet 310 including folding of the first ground plane layer 311 and the second ground plane layer 312. The sensor sheet 310 includes a middle section consisting of a first 313 and second 314 array of capacitive touch pads, similar to the sensor sheet 300. In the embodiment shown, the first 311 and second 312 ground plane layers are attached to the sensor sheet 300 at respective top and bottom ends. The first 311 and second 312 ground plane layers can be folded backward at their respective attachments in order to lay over the outer side of the sensor sheet, as illustrated in FIG. 3C. In particular, as shown in FIG. 3C, the first ground plane layer 311 can be folded back over the outer side of the sensor sheet 310 substantially parallel to the first array of capacitive touch pads 313. Similarly, the second ground plane layer 312 can be folded back over the outer side of the sensor sheet 300 substantially parallel to the second array of capacitive touch pads 314. On the side of the sensor sheet 300 closest to the first 311 and second 312 ground plane layers 312 there is a dielectric separator layer 316, as described above with reference to the sensor sheet 210. The separator layer 316 may have adhesives (e.g., glue or tape) on both sides, such that the first 311 and second 312 ground plane layers can firmly attach to the back of the sensor sheet 310 once fully folded.

In the embodiment shown in FIGS. 3B and 3C, the first ground plane layer 311 and the second ground plane layer 312 are comprised of conductive material arranged in a grid pattern, similarly to the six capacitive touch pads of both the first 313 and second 314 arrays of capacitive touch pads. In contrast to the capacitive touch pads of the first 313 and second 314 arrays, the first 311 and second 312 ground plane layers are each represented as single, larger grids of conductive material. The first 311 and second 312 ground plane layers are each connected to respective ribbon connectors of the ribbon connectors 315, which can be connected to a capacitive sensor chip driver of a PCB (e.g., like the ribbon connectors 305). In other embodiments than those depicted in FIGS. 3B and 3C, the sensor sheet 310 may include bigger or smaller ground plane layers, or the ground plane layers may include a different arrangement of conductive material. Furthermore, the sensor sheet 310 is depicted with first 313 and second 314 arrays of capacitive touch pads that are similar to the first 303 and second 304 arrays of capacitive touch pads of the sensor sheet 300 for the purposes of illustration only, and one skilled in the art will appreciate that one or more ground plane layers can be similarly applied to other sensor sheets, such as those depicted in FIG. 3D-G or 4B.

Figure 3D:
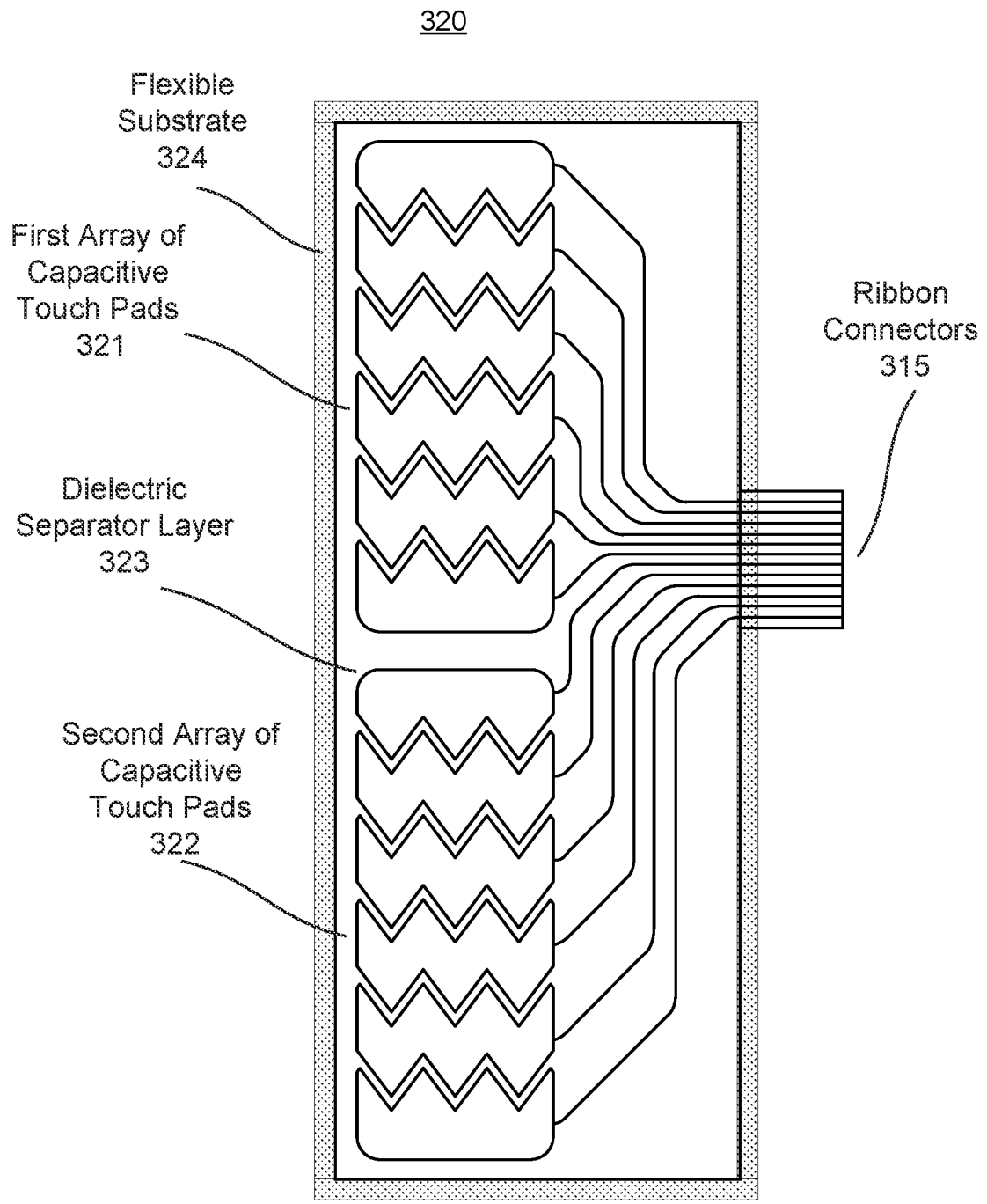
FIG. 3D illustrates a sensor sheet including first and second arrays of capacitive touch pads comprising conductive material arranged in a zig-zag pattern, according to one embodiment.

FIG. 3D illustrates an embodiment of a sensor sheet 320 including first 321 and second 322 arrays of capacitive touch pads comprising conductive material arranged in a zig-zag pattern. In comparison to the sensor sheets 300 and 320, the capacitive touch pads of the first 321 and second 322 arrays cover smaller regions of the sensor sheet 320 but are more densely filled by conductive material. As such, the first 321 and second 322 arrays of capacitive touch pads advantageously increase capacitance sensitivity and reduce the amount of conductive material required (e.g., reducing manufacturing costs). In an alternative embodiment, the sharp edges of the capacitive touch pads created by the zig-zag patterns are rounded (e.g., to edges with a radius of 1-2 mm), which mitigates electromagnetic interference. As with the sensor sheet 300, the sensor sheet 320 includes a dielectric separator layer 323 which is overlaid below a flexible substrate 324 and the first 321 and second 322 arrays of capacitive touch pads. Furthermore, the first 321 and second 322 arrays of capacitive touch pads are separated by a gap where the sensor sheet 320 can be folded so the first 321 and second 322 arrays of capacitive touch pads are substantially parallel to each other, and the first and second arrays of capacitive touch pads are connected to the ribbon connectors 325.

Figure 3E:
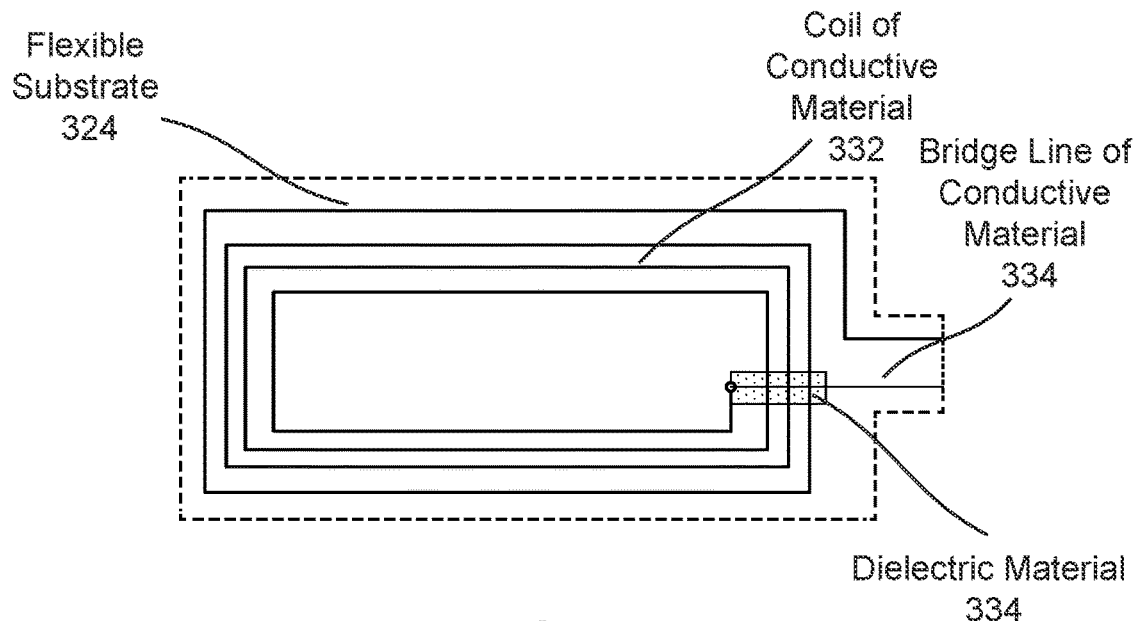
FIG. 3E illustrates a sensor sheet including a flexible substrate overlaid by a coil of conductive material, according to one embodiment.
Figure 3F:
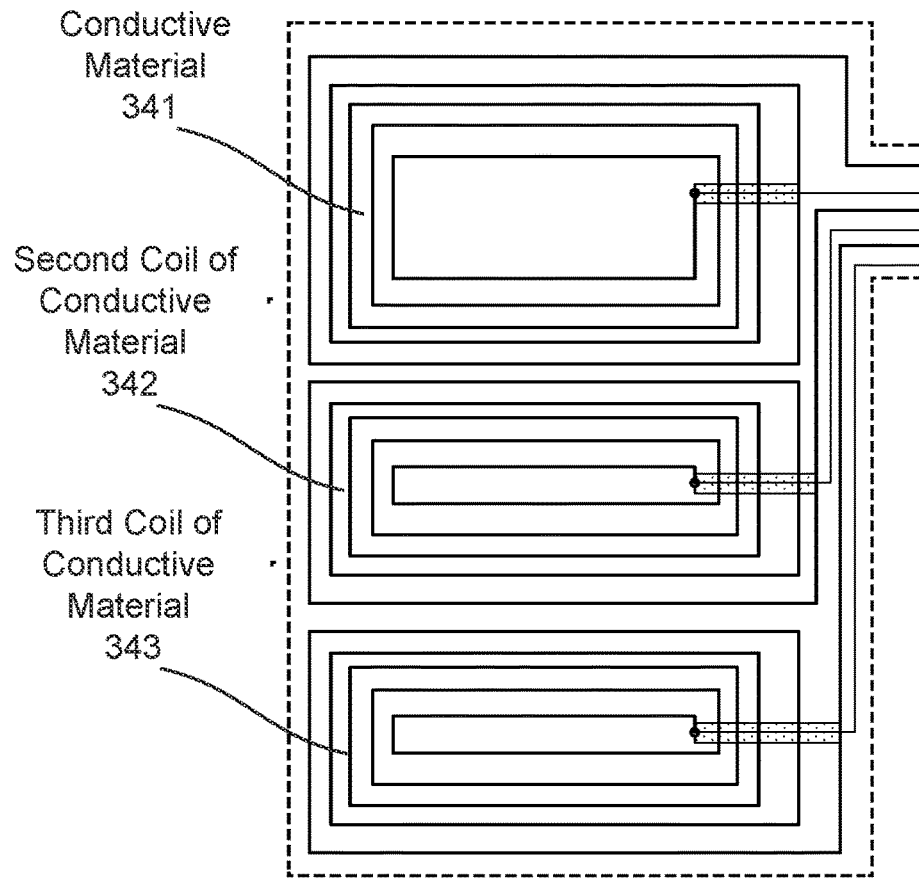
FIG. 3F illustrates a sensor sheet including multiple coils of conductive material, according to one embodiment.

FIGS. 3E-F illustrate embodiments of sensor sheets that can function as either a capacitive sensor or an inductive sensor, either separately or in parallel. FIG. 3E particularly illustrates an embodiment of a sensor sheet 330 including a flexible substrate 331 overlaid by a coil of conductive material 332 (e.g., a conductive trace). The coil of conductive material 332 has a first end that can be connected to a first terminal of an inductive sensor driver chip (e.g., on a PCB) and a second end at the center of the coil 332. The second end of the coil 332 is connected to a bridge line of conductive material 333 that passes back over the outer loops of the coil, which can be connected to a second terminal of the inductive sensor driver chip. In addition to the inductive driver chip, either the first or second end of the coil 332 can further be connected to a capacitive driver chip (e.g., the sensor driver chip 225). The capacitive and inductive driver chips function can be provided by one system on chip (SoC) or integrated circuit (IC) solution, or be working separately as one capacitive sensor driver chip and one inductive sensor driver chip connected to and coordinated by a microcontroller (e.g., the microcontroller 230) via dedicated communication channels (e.g., digital I/O ports or serial communication bus like I2C, SPI, I2S etc.). A dielectric material 334 is positioned between the bridge line 333 and the coil 332 in order to act as an insulator and prevent a short circuit. The coil 331 is printed or otherwise affixed directly to the flexible substrate 331. Similarly, the dielectric material 334 is printed or otherwise affixed on top of the coil 332, and the bridge line 333 is printed or otherwise affixed on top of the dielectric material 334 or the flexible substrate 331 at the relevant portions of the sensor sheet 330.

The coil 332 can alternate between a capacitive and inductive sensor by connecting one end of the coil 332 to a terminal of a capacitive sensor driver chip and both the first and second ends of the coil 332 to an inductive sensor driver chip. In particular, when the first and second end of the coil are shorted, the coil 332 acts as a capacitive sensor. Similarly, when the first and second end of the coil 332 are not shorted, the coil 332 acts as an inductive sensor. Switching between a capacitive sensor and an inductive sensor may be controlled by a microcontroller connected to the inductive and capacitive sensor driver chips (e.g., the microcontroller 230). In this case, the microcontroller may process capacitance measurements or electrical current measurements obtained using the capacitance sensor or inductive sensor, respectively, in order to detect blister pill packs, as described above with reference to the blister pill pack container apparatus 200. For instance, an oscillating electrical current of the coil 331 functioning as an inductive sensor can be influenced by a frangible aluminum layer of a blister pill pack in contact with or in proximity to the coil 331 (e.g., passing through a magnetic field produced by the coil 331). The microcontroller can process changes to the oscillating electrical current of the coil 331 (e.g., a rate of change of the frequency of the current or direction of the current) to detect a blister pill pack or determine other information, e.g., a movement direction or speed of the blister pill pack.

FIG. 3F illustrates an embodiment of a sensor sheet 340 including multiple coils of conductive material (e.g., the coils 341, 342, and 343). In the embodiment shown, each of the coils 341, 342, and 343 are like the coil 331 depicted in FIG. 3D. By connecting the first and second ends of the coils 341, 342, and 343 to inductive and capacitive sensor driver chips in the manner described above with reference to the sensor sheet 330, the sensor sheet 340 can be used as both a capacitive and inductive sensor at the same time. As such, a microcontroller may process both electrical current measurements and capacitance measurements together in order to improve the accuracy of blister pill pack detections. A capacitive sensor driver chip and an inductive sensor driver chip can be applied to drive the coils 341, 342, and 343 in manners similar to what is described above with reference to FIG. 3E. Similarly to the sensor sheet 330, the capacitive and inductive driver chips function can be provided by one system on chip (SoC) or integrated circuit (IC) solution, or be working separately as one capacitive sensor driver chip and one inductive sensor driver chip connected to and coordinated by the microcontroller 230 via dedicated communication channels.

Figure 3G:
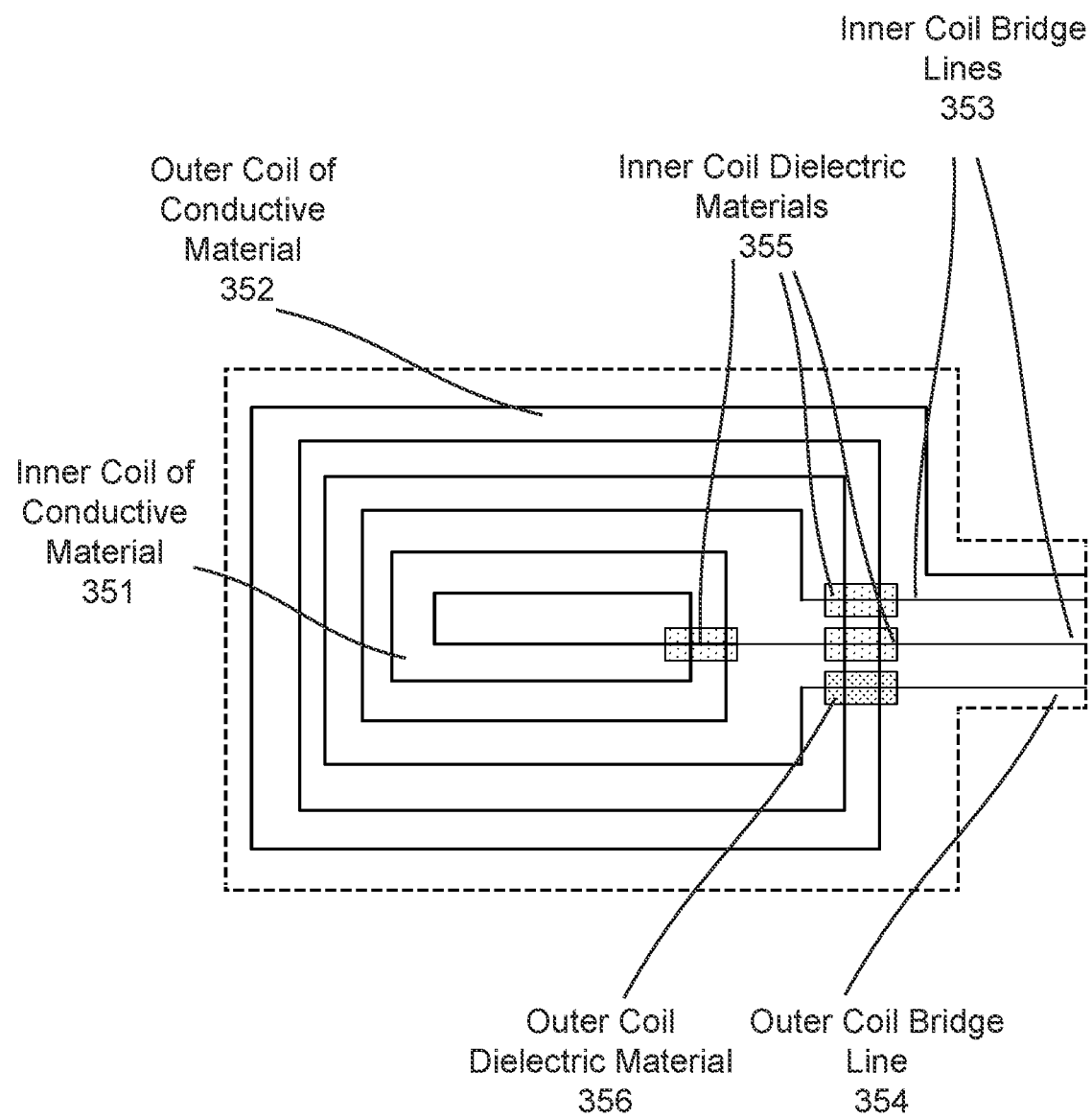
FIG. 3G illustrates a sensor sheet including an inner coil of conductive material and an outer coil of conductive material, according to one embodiment.

FIG. 3G illustrates an embodiment of a sensor sheet 350 including an inner coil of conductive material 351 and an outer coil of conductive material 352. In the embodiment shown, the inner coil 351 and the outer coil 352 are like the coil 331 depicted in FIG. 3D. However, in contrast with the coil 331, the sensor sheet includes additional bridge lines (e.g., inner coil bridge lines 353 and the outer coil bridge line 354) in order to accommodate the first and second ends of the inner coil 351 and outer coil 352. Similarly to the coil 331, in between the inner coil bridge lines 353 and the outer coil bridge line 354 are the respective inner coil dielectric materials 355 and outer coil dielectric material 356. The inner coil 351 and the outer coil 352 may both alternate between functioning as capacitive sensors or inductive sensors, as described above with reference to the coil 331. For example, the inner coil 351 may function as an inductive sensor and the outer coil 352 may each function as a capacitive sensor, or vice versa. Alternatively, the inner coil 351 and outer coil 352 can both function as inductive sensors at one time and both function as capacitive sensors at another time.

In an alternative embodiment to that depicted in FIGS. 3E-G, one or more coils of the sensor sheets 330, 340, or 350 is a compressed solenoid that is rolled up to form a sleeve where a blister pill pack can be inserted. In alternate embodiments, the compressed solenoid may be structured in other volumetric geometry to form a sleeve.

Figure 4A:
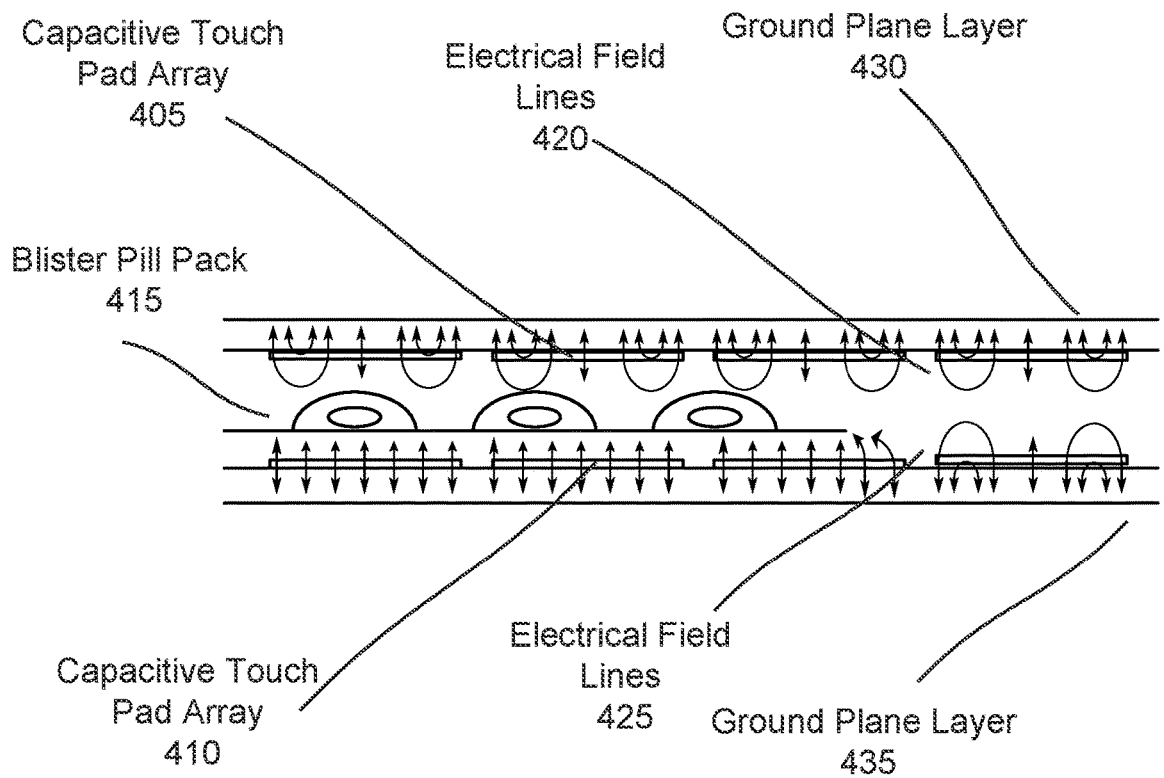
FIG. 4A illustrates detection of a blister pill pack by substantially parallel capacitive touch pad arrays of a sensor sheet, according to one embodiment.
Figure 4B:
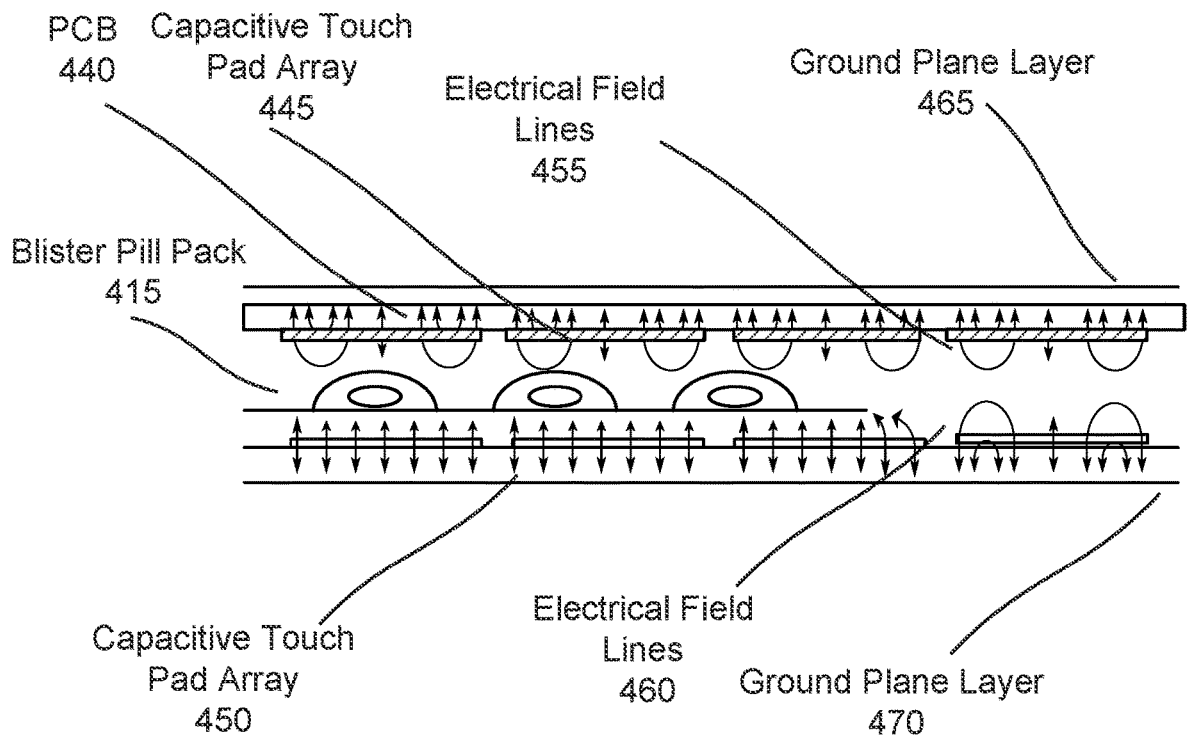
FIG. 4B illustrates detection of the blister pill pack by a substantially parallel capacitive touch pad array of a PCB and a capacitive touch pad array of a sensor sheet, according to one embodiment.

FIGS. 4A-B illustrate embodiments of blister pill pack detection via substantially parallel capacitive touch pad arrays. FIG. 4A particularly illustrates an embodiment of detection of a blister pill pack 415 by substantially parallel capacitive touch pad arrays 405 and 410 of a sensor sheet (e.g., the sensor sheet 210). In the embodiment shown, electrical field lines 420 and 425 generated by the capacitive touch pad arrays 405 and 410 respectively (illustrated by arrows representing imaginary direction vectors of the electrical fields 420 and 225) are influenced based on the presence of the blister pill pack 415. Generally, the electrical field lines 420 and 225 are directed to the ground plane layers 430 and 435, respectively. However, the bottom side of the blister pill pack 415 is comprised of aluminum foil that attracts the electric field 425 generated by the closest capacitive touch pad array (i.e., the capacitive touch pad array 410). Based on analog capacitance signals received by the capacitive touch pad array 410 indicating the attraction of the electric field 425 to the blister pill pack 415, the blister pill pack 415 can be detected (e.g., by the microcontroller 230 of the PCB 220). In particular, the position, direction, or speed of movement of the blister pill pack 415 can be determined, or the orientation of the blister pill pack 415 (i.e., that the bottom side of the blister pill pack 415 is closest to the capacitive touch pad array 410).

In an alternative embodiment than that depicted in FIG. 4A, one or more capacitive touch pad arrays are positioned only on one side of the blister pill pack 415 (e.g., only the capacitive touch pad array 410). For example, only the capacitive touch pad array 410 may be present. In this case, portions of the electrical field 425 on the side of the sensor sheet opposite the ground plane layer 435 are directed away from the ground plane layer 435.

FIG. 4B particularly illustrates an embodiment of detection of the blister pill pack 415 by a substantially parallel capacitive touch pad array 445 of a PCB 440 and a capacitive touch pad array 450 of a sensor sheet. In the embodiment shown, the capacitive touch pads 445 of the PCB 440 are comprised of copper touch pads etched onto the surface of the PCB 440. The sensor sheet including the capacitive touch pad array 450 and the PCB 440 may be attached in the middle and folded, similarly to the sensor sheet 400. The PCB 440 may further be comprised of additional components, such as the sensor driver chip 225 or the microcontroller 230, as in the case of the PCB 220. Alternatively, the sensor sheet including the capacitive touch pad array 450 and the PCB 440 may be separate components. As described above with reference to the sensor sheet 400, electrical field lines 455 and 460 generated by the capacitive touch pad arrays 445 and 450 are primarily directed to the ground plane layers 465 and 470, respectively. The ground plane layer 465 can be edged directly onto the PCB 440 or be a separate layer. However, the electrical field lines 460 are influenced based on the presence of the blister pill pack 415. The blister pill pack 415 can further be detected based on analog capacitance signals received by either the capacitive touch pad arrays 445 or 450 depending on the orientation of the blister pill pack 415 and resulting influence of the electrical field lines 455 and 460.

In an alternative embodiment to that depicted in FIG. 4B, the sensor sheet including the capacitive touch pad array 450 may also be a PCB. In particular, as described above with reference to the sensor sheet 210, either the PCB 440 or the sensor sheet may be comprised of a rigid or flexible PCB material. In one embodiment, the PCB 440 and the sensor sheet may be two ends of a folded sheet of flexible PCB material, e.g., like the folded sensor sheet 210 depicted in FIG. 2A.

Exemplary Housing Embodiments

Figure 5:
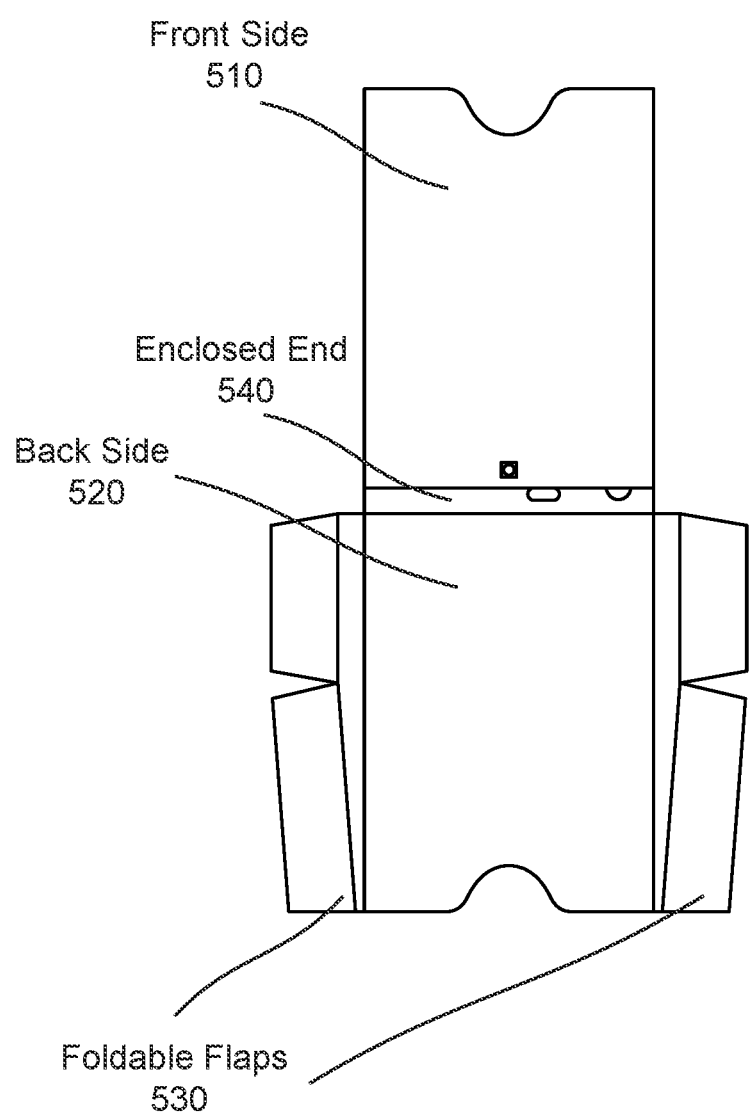
FIG. 5 illustrates a deconstructed housing for a blister pill pack container apparatus, according to one embodiment.

FIG. 5 illustrates an embodiment of a deconstructed housing 500 for a blister pill pack container apparatus. In the embodiments shown, the housing 500 is depicted deconstructed for the purposes of illustration only, and the housing 500 can be appropriately folded or otherwise constructed or configured in order to fully or partially enclose other components of the pill pack container apparatus. The housing 500 includes a front side 510 and a back side 520. The terms "front side" and "back side" are used for the purpose of illustration only, and the two sides of the housing 500 may be oriented in any suitable manner. The back side 520 is connected to foldable flaps 530, which can be folded over the inner components of the blister pill pack container apparatus (e.g., a sensor sheet, PCB, or power source) in order to hold the inner components in place. Between the front side 510 and the back side 520 is an enclosed end 540 of the housing 500. The enclosed end 540 of the housing 500 includes openings where one or more terminals of a component of the blister pill pack container apparatus can be accessed (e.g., a plugin terminal of a power source). The front side 510 also includes an opening where an LED light component of the blister pill pack container apparatus can be visible to a user of the blister pill pack apparatus (e.g., as described above with reference the PCB 220). In other embodiments than the one shown in FIG. 5, the housing may have other openings to show other components of the blister pill pack container apparatus or showing a space where a blister pill pack can be inserted (e.g., for a user to view or touch the blister pill pack). The front side and back side are curved on the ends which forms a closeable end when the housing 500 is constructed. In other embodiments than the one shown in FIG. 5, the closable end can have a different structure, such as two straight ends of the front side 510 and the back side 520 (e.g., edges without curves, as depicted in FIGS. 1 and 2B).

The housing 500 is comprised of a cuttable flexible material (e.g., paper, PET, PE, PC, or PVC). The cuttable flexible material is advantageously cheaper to manufacture in comparison to processes like injection molding. As a further advantage, printing designs onto the cuttable flexible material is easier than alternative materials. Furthermore, durable materials such as plastic can be laminated onto the housing 500 to enhance its durability, temperature, dust and sand tolerance, and water resistance.

The housing 500 can further be manufactured using an injection mold or with hard or rigid materials. A hard-shell housing 500 can advantageously prevent external objects from bending the shape of the housing 500, which could trigger a sensor sheet within the housing 500 to produce false positive results. Furthermore, a hard-shell housing 500 protects the battery and other fragile components inside the housing 500 from being smashed or punctured by external objects.

Additional Configuration Considerations

The disclosed configurations provide a number of advantages over existing container apparatuses. For example, the flexibility of described sensor sheets allows for the object container apparatus to house or detect objects with various shapes or structures (e.g., blister pill packs with a variety of characteristics). Furthermore, the positioning of arrays of capacitive touch pads on both sides of a space where an object can be inserted provides for improved object detection, such as detecting objects irrespective of object orientation or additionally determining the orientation of a detected object. Additionally, the modular design of described object container apparatuses allows for various components to be reconfigured, such as using different sensor sheets or housings. Moreover, the configuration of one or more touch pad arrays on the sensor sheet allow detections to be made even when the blister pill pack is not slid all the way in or out of the housing of the blister pill pack container apparatus (e.g., all the way into the space between substantially parallel arrays of capacitive touch pads). Among other advantages, this provides for an improved user experience. For example, users of the described container apparatuses do not need to fully remove or insert a blister pill pack for the sensor sheet to receive capacitance signals enabling described functionality, e.g., allowing users to take medications discretely.

Throughout this specification, some embodiments have used the expression "coupled" along with its derivatives. The term "coupled" as used herein is not necessarily limited to two or more elements being in direct physical or electrical contact. Rather, the term "coupled" may also encompass two or more elements are not in direct contact with each other, but yet still co-operate or interact with each other, or are structured to provide a thermal conduction path between the elements.

Likewise, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Upon reading this disclosure, those of skill in the art will appreciate still additional alternative structural and functional designs for an object container apparatus or other apparatuses as disclosed from the principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The invention claimed is:

1. A blister pill pack container apparatus, comprising:
a housing having a first side and a second side,
the first side having a first end and a second end and the second side having a first end and a second end, the first end of the first side and the first end of the second side forming an enclosed end of the housing and the second end of the first side and the second end of the second side forming a closeable end of the housing,
the first side having an exterior surface and an interior surface and the second side having an exterior surface and an interior surface, the exterior surface of the first side and the exterior surface of the second side forming an exterior of the housing and the interior surface of the first side and the interior surface of the second side forming a cavity, the cavity having:
  a sensor sheet attached to the interior surface of the first side and the interior surface of the second side, the sensor sheet comprising a flexible substrate and a first and second array of capacitive touch pads positioned on the flexible substrate, the capacitive touch pads of the first and second arrays comprising one or more layers of conductive material, the flexible substrate folded to arrange the first array of capacitive touch pads substantially parallel to the second array of capacitive touch pads with a space between the first and second array of capacitive touch pads for inserting a blister pill pack within the cavity;
  a printed circuit board (PCB) positioned between the sensor sheet and the interior surface of the first or second sides, the PCB comprising:
    a capacitive sensor driver chip coupled with the first array and the second array of capacitive touch pads, the capacitive sensor driver chip having a terminal to receive at least a first and a second capacitance signal from the first and the second array of capacitive touch pads; and
    a microcontroller configured to process a change between the first and the second capacitance signals to detect and measure movement of a blister pill pack sliding in to and out of the space.

2. The blister pill pack container apparatus of claim 1, wherein the conductive material comprises one or more of a silver based conductive paint layer, carbon-based conductive paint layer, copper tape layer, or conductive graphite ink layer.

3. The blister pill pack container apparatus of claim 1, wherein the first or second array of capacitive touch pads each comprise one or more strips of the one or more layers of conductive material, the strips arranged on the flexible substrate in parallel to the folding of the flexible substrate layer.

4. The blister pill pack container apparatus of claim 3, wherein the one or more strips of the one or more layers of conductive material are structured using one or more of a grid pattern, a solid fill pattern, or a zig-zag pattern.

5. The blister pill pack container apparatus of claim 1, further comprising:

first and second ground plane layers respectively positioned between the sensor sheet and the interior surfaces of the first and second sided of the housing, the first and second ground plane layers comprising one or more additional layers of conductive material and coupled with the capacitive sensor chip.

6. The blister pill pack container apparatus of claim 5, wherein the first and second ground plane layers are attached at respective first and second ends of the sensor sheet, where the first and second ground plane layers are folded back where attached toward the enclosed first end of the housing.

7. The blister pill pack container apparatus of claim 1, wherein the sensor sheet further comprises an insulation layer applied over the one or more layers of conductive material.

8. The blister pill pack apparatus container of claim 1, wherein the microcontroller is further configured to process the change between the first and the second capacitance signals to determine one or more of an orientation of the blister pill pack in the space, a movement speed of the blister pill pack in the space, a movement direction of the blister pill pack in the space, or a position of the blister pill pack in the space.

9. The blister pill pack container apparatus of claim 1, wherein the one or more layers of conductive material of the sensor sheet are structured to receive the first and second capacitance signals localized to an individual blister of the blister pill pack, and wherein the microcontroller is further configured to process the change between the first and the second capacitance signals localized to the individual blister to determine a presence or absence of a pill within the individual blister.

10. The blister pill pack container apparatus of claim 1, wherein the PCB further comprises a communication module that enables communication between the microcontroller and a computing device, wherein the microcontroller is further configured to transmit information corresponding to the detection of the blister pill pack to the computing device.

11. The blister pill pack container apparatus of claim 1, further comprising:
an acceleration sensor coupled to the microcontroller, wherein the acceleration sensor is configured to receive first and second acceleration signals derived from the acceleration sensor, and wherein the microcontroller is further configured to:
process a change between the first and second acceleration signals to detect a presence or absence of user interaction with the blister pill pack container apparatus; and
reduce power consumption associated with the sensor sheet responsive to detecting the absence of user interaction based on the change between the first and second acceleration signals.

12. The blister pill pack container apparatus of claim 1, further comprising:
one or more magnets positioned within the cavity or at or near the closeable end of the housing; and
a hall-effect sensor coupled to the one or more magnets and the microcontroller, wherein the hall-effect sensor is configured to receive first and second magnetic field signals from the one or more magnets, and wherein the microcontroller is further configured to process a change between the first and second magnetic field signals to detect user interaction with the blister pill pack container apparatus.

13. The blister pill pack container apparatus of claim 1, further comprising:

a sound sensor coupled to the microcontroller, wherein the sound sensor is configured to output a sound signal and receive a reflected sound signal responsive to reflection of the output sound signal off of a surface, and wherein the microcontroller is further configured to process the output sound signals and the reflected sound signal to detect a blister pill pack in the space.

14. The blister pill pack container apparatus of claim 1, further comprising:
an infrared (IR) sensor coupled to the microcontroller and attached to the interior surfaces of the first and second side of the housing in proximity to the closeable second end, wherein the IR sensor is configured to receive first and second IR signals, and wherein the microcontroller is further configured to process the first and second IR signals to detect a blister pill pack in proximity to the closable second end.

15. The blister pill pack container apparatus of claim 1, further comprising:
a resistive sensor positioned within the cavity and coupled to the microcontroller, wherein the microcontroller is further configured to process a change in a switch state of the resistive sensor to detect a blister pill pack in the space.

16. The blister pill pack container apparatus of claim 1, wherein the PCB further comprises an inductive sensor driver chip having a plurality of terminals, and wherein the first or second array of capacitive touch pads comprise:
a coil of the one or more layers of conductive material configurable as a capacitive touch pad and inductive sensor, the coil comprising a first end coupled to a first terminal of the plurality of terminals and a second end coupled to a bridge line, the bridge line overlaying the coil and connected to a second terminal of the plurality of terminals; and
a piece of dielectric material positioned between the coil and the bridge line.

17. The blister pill pack container apparatus of claim 16, wherein the first or second array of capacitive touch pads further comprise:
an additional coil of the one or more layers of conductive material configurable as a capacitive touch pad and inductive sensor, the additional coil positioned inside the center of the coil and comprising a first end coupled to a third terminal of the plurality of terminals and a second end coupled to an additional bridge line, the additional bridge line overlaying the coil and the additional coil and connected to a fourth terminal of the plurality of terminals; and
a plurality of additional pieces of dielectric material positioned between the additional bridge line and the coil and positioned between the additional bridge line and the additional coil.

18. A blister pill pack apparatus, comprising:
a housing having one or more interior surfaces forming a cavity, the cavity having:
one or more sensor sheets attached to the one or more interior surfaces, the one or more sensor sheets comprising at least a first and second array of capacitive touch pads comprising one or more layers of conductive material, the one or more sensor sheets arranged to position the first array of capacitive touch pads substantially parallel to the second array of capacitive touch pads with a space between the first and second array of capacitive touch pads for inserting a blister pill pack within the cavity;

a capacitive sensor driver chip coupled with the one or more arrays of capacitive touch pads, the capacitive sensor driver chip having a terminal to receive at least a first and a second capacitance signal from the one or more arrays of capacitive touch pads; and a microcontroller configured to process a change between the first and the second capacitance signals to detect and measure movement of a blister pill pack sliding in to and out of the space.

19. The blister pill pack apparatus of claim 18, wherein a first sensor sheet of the one or more sensor sheets is comprised of a sheet of flexible PCB material, wherein the first array of capacitive touch pads is etched on the sheet of flexible PCB material.

20. The blister pill pack apparatus of claim 19, wherein the sheet of flexible PCB material comprises an integrated circuit including the capacitive sensor driver chip and the microcontroller.

21. The blister pill pack apparatus of claim 19, wherein the second array of capacitive touch pads is further etched on the sheet of flexible PCB material and the sheet of flexible PCB material is folded in order to arrange the first array of capacitive touch pads substantially parallel to the second array of capacitive touch pads.

* * * * *

UNITED STATES PATENT AND TRADEMARK OFFICE
CERTIFICATE OF CORRECTION

| | |
|---|---|
| PATENT NO. | : 11,766,384 B2 |
| APPLICATION NO. | : 17/108573 |
| DATED | : September 26, 2023 |
| INVENTOR(S) | : Jiun Lang Wong |

It is certified that error appears in the above-identified patent and that said Letters Patent is hereby corrected as shown below:

In the Claims

In Column 23, in Claim 8, Line 16, delete "apparatus container" and insert -- container apparatus --, therefor.

Signed and Sealed this
Eighth Day of October, 2024

Katherine Kelly Vidal
*Director of the United States Patent and Trademark Office*